(12) United States Patent  (10) Patent No.: US 8,469,983 B2
Fung et al.  (45) Date of Patent: Jun. 25, 2013

(54) DEVICES AND METHODS FOR REMOTE SUTURE MANAGEMENT

(75) Inventors: Gregory W. Fung, San Mateo, CA (US); Eduardo Sager, Milpitas, CA (US); Russell A. Seiber, Redwood Shores, CA (US); Gary H. Miller, Milpitas, CA (US); Maria Garcia, San Jose, CA (US)

(73) Assignee: SentreHEART, Inc., Redwood City, CA (US)

( * ) Notice: Subject to any disclaimer, the term of this patent is extended or adjusted under 35 U.S.C. 154(b) by 368 days.

(21) Appl. No.: 12/212,511

(22) Filed: Sep. 17, 2008

(65) Prior Publication Data

US 2009/0082797 A1 Mar. 26, 2009

Related U.S. Application Data

(60) Provisional application No. 60/974,051, filed on Sep. 20, 2007.

(51) Int. Cl.
*A61B 17/138* (2006.01)

(52) U.S. Cl.
USPC .......................................... 606/170; 606/138

(58) Field of Classification Search
USPC ................. 606/138–139, 144–148, 159, 167, 606/170, 222, 83; 604/22
See application file for complete search history.

(56) References Cited

U.S. PATENT DOCUMENTS

| | | | |
|---|---|---|---|
| 3,496,932 A | 2/1970 | Prisk et al. | |
| 3,802,074 A * | 4/1974 | Hoppe | ............................ 30/134 |
| 3,841,685 A | 10/1974 | Kolodziej | |
| 3,999,555 A | 12/1976 | Person | |
| 4,030,509 A | 6/1977 | Heilman et al. | |
| 4,078,305 A * | 3/1978 | Akiyama | ........................ 30/134 |
| 4,181,123 A | 1/1980 | Crosby | |

(Continued)

FOREIGN PATENT DOCUMENTS

| | | |
|---|---|---|
| EP | 0 598 219 A2 | 5/1994 |
| EP | 0 598 219 A3 | 5/1994 |

(Continued)

OTHER PUBLICATIONS

Non-Final Office Action mailed on Mar. 13, 2008 for U.S. Appl. No. 10/963,371, filed Oct. 11, 2004, 13 pages.

(Continued)

*Primary Examiner* — Ryan Severson
*Assistant Examiner* — Rachel S Papeika
(74) *Attorney, Agent, or Firm* — Morrison & Foerster LLP

(57) ABSTRACT

Described here are devices and methods for suture management. In some variations, the devices comprise an elongate tubular member having a proximal end, a distal end, a lumen therebetween, a cantilever blade positioned near the distal end of the elongate tubular member, and an expandable member positioned adjacent the cantilever blade for actuating the cantilever blade. Also described are devices comprising an elongate tubular member having a proximal end, a distal end, a lumen at least partially therebetween, and an aperture in a wall thereof for passage of a suture therethrough. These devices further comprise a blade connected to a blade housing disposed within the lumen, where the blade is oriented parallel to the longitudinal axis of the lumen. The blade and blade housing may be slidable within the lumen, or an inner shaft for may be slidable within the lumen. Methods of using the devices are also described.

5 Claims, 16 Drawing Sheets

U.S. PATENT DOCUMENTS

| | | | |
|---|---|---|---|
| 4,249,536 A | 2/1981 | Vega |
| 4,257,278 A | 3/1981 | Papadofrangakis et al. |
| 4,319,562 A | 3/1982 | Crosby |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,226,535 A | 7/1993 | Roshdy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,252 A | 8/1994 | Cohen |
| 5,385,156 A | 1/1995 | Oliva |
| 5,387,219 A | 2/1995 | Rappe |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,367 A | 9/1995 | Kadry |
| 5,498,228 A | 3/1996 | Royalty et al. |
| 5,540,711 A | 7/1996 | Kieturakis et al. |
| 5,591,177 A | 1/1997 | Lehrer |
| 5,609,597 A | 3/1997 | Lehrer |
| 5,624,430 A | 4/1997 | Eton et al. |
| 5,634,895 A | 6/1997 | Igo et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,895,298 A | 4/1999 | Faupel et al. |
| 5,897,586 A | 4/1999 | Molina |
| 5,900,433 A | 5/1999 | Igo et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,570 A | 4/2000 | Epstein et al. |
| 6,048,329 A | 4/2000 | Thompson et al. |
| 6,059,750 A | 5/2000 | Fogarty et al. |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,561,969 B2 | 5/2003 | Frazier et al. |
| 6,592,552 B1 | 7/2003 | Schmidt |
| 6,610,055 B1 | 8/2003 | Swanson et al. |

| | | |
|---|---|---|
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,331,979 B2 | 2/2008 | Khosravi et al. |
| 7,608,091 B2 | 10/2009 | Goldfarb et al. |
| 7,722,641 B2 | 5/2010 | van der Burg et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 2001/0025132 A1 | 9/2001 | Alferness et al. |
| 2002/0017306 A1 | 2/2002 | Cox et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0083542 A1 | 5/2003 | Alferness et al. |
| 2003/0083674 A1* | 5/2003 | Gibbens, III .................. 606/144 |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1 | 3/2004 | Burbank et al. |
| 2004/0064138 A1 | 4/2004 | Grabek |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043745 A1 | 2/2005 | Alferness et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0154404 A1 | 7/2005 | Liddicoat |
| 2005/0165466 A1 | 7/2005 | Morris et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0212045 A1* | 9/2006 | Schilling et al. .................. 606/138 |
| 2006/0247672 A1 | 11/2006 | Vidlund et al. |
| 2006/0253128 A1 | 11/2006 | Sekine et al. |
| 2006/0253129 A1 | 11/2006 | Liddicoat et al. |
| 2007/0016228 A1 | 1/2007 | Salas |
| 2007/0027456 A1 | 2/2007 | Gartner et al. |
| 2007/0060951 A1 | 3/2007 | Shannon |
| 2007/0073313 A1 | 3/2007 | Liddicoat et al. |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270891 A1 | 11/2007 | McGuckin, Jr. |
| 2008/0009843 A1 | 1/2008 | de la Torre |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0097489 A1 | 4/2008 | Goldfarb et al. |
| 2008/0147097 A1 | 6/2008 | Liddicoat et al. |
| 2008/0221593 A1 | 9/2008 | Liddicoat et al. |
| 2008/0228265 A1* | 9/2008 | Spence et al. .................. 623/2.36 |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0143791 A1 | 6/2009 | Miller et al. |
| 2009/0157118 A1 | 6/2009 | Miller et al. |
| 2010/0069925 A1 | 3/2010 | Friedman et al. |
| 2010/0174296 A1 | 7/2010 | Vakharia et al. |
| 2011/0087247 A1 | 4/2011 | Fung et al. |

FOREIGN PATENT DOCUMENTS

| | | |
|---|---|---|
| EP | 0 598 219 B1 | 5/1994 |
| EP | 1 010 397 A1 | 11/1999 |
| GB | 1 506 142 A | 4/1978 |
| JP | 11-507262 A | 6/1999 |
| JP | 2001-120560 A | 5/2001 |
| JP | 2002-540901 A | 12/2002 |
| WO | WO-94/01045 A1 | 1/1994 |
| WO | WO-94/04079 A1 | 3/1994 |
| WO | WO-94/08514 A1 | 4/1994 |
| WO | WO-96/40356 A1 | 12/1996 |
| WO | WO-97/11644 A1 | 4/1997 |
| WO | WO-97/43957 A1 | 11/1997 |
| WO | WO-00/61202 A1 | 10/2000 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034767 C2 | 4/2005 |
| WO | WO-2005/034802 A2 | 4/2005 |
| WO | WO-2005/034802 A3 | 4/2005 |
| WO | WO-2006/110734 A2 | 10/2006 |
| WO | WO-2006/115689 A1 | 11/2006 |
| WO | WO-2007/056502 A1 | 5/2007 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |

| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |

OTHER PUBLICATIONS

Non-Final Office Action mailed on Aug. 6, 2008 for U.S. Appl. No. 10/963,371, filed Oct. 11, 2004, 14 pages.

U.S. Appl. No. 12/363,359, filed Jan. 30, 2009, for Miller et al.

U.S. Appl. No. 12/363,381, filed Jan. 30, 2009, for Miller et al.

Final Office Action mailed on Jun. 22, 2009, for U.S. Appl. No. 10/963,371, filed Oct. 11, 2004, 11 pages.

Johnson, W.D. et al. (2000). "The Left Atrial Appendage: Our Most Lethal Human Attachment! Surgical Implications," *Euro. J. Cardiothoracic. Surg.* 17:718-722.

Kirkorian, J.G. et al. (Nov. 1978). "Pericardiocentesis," *Am. J. Med.* 65(5):808-814.

Non-Final Office Action mailed on Jun. 26, 2009, for U.S. Appl. No. 11/600,671, filed Nov. 15, 2006, 9 pages.

Afibfacts.Com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 2006: 1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Bonanomi, G. et al. (Jan. 1, 2003). "Left Atrial Appendectomy and Maze," *Journal of the American College of Cardiology* 41(1):169-171.

Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.

Botham, R.J. et al. (May 1959). "Pericardial Tamponade Following Percutaneous Left Ventricular Puncture," *Circulation* 19:741-744.

Brock, R. et al. (1956). "Percutaneous Left Ventricular Puncture in the Assessment of Aortic Stenosis," *Thorax* 11:163-171.

Burke, R.P. et al. (1992). "Improved Surgical Approach to Left Atrial Appendage Aneurysm," *Journal of Cardiac Surgery* 7(2):104-107.

Canaccord Adams (Aug. 11, 2008). "A-Fib: Near A Tipping Point," 167 pages.

Chung, M.K. (Jul. 2003). "Current Clinical Issues in Atrial Fibrillation," *Cleveland Clinic Journal of Medicine* 70(Supp. 3):S6-S11.

Coffin, L.H. (Jun. 1985). "Use of the Surgical Stapler to Obliterate the Left Atrial Appendage," *Surgery, Gynecology & Obstetric* 160:565-566.

Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.

Costa, R. et al. (2006). "Bi-Atrial Subxiphoid Epicardial Pacemaker in Superior Vena Cava Syndrome," *Arq. Bras. Cardiol.* 87:e45-e47.

Cox, J.L. et al. (2004). "The Role of Surgical Intervention in the Management of Atrial Fibrillation," *Texas Heart Institute Journal* 31(3):257-265.

Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.

D'Avila, A. et al. (Apr. 2003). "Pericardial Anatomy for the Interventional Electrophysiologist," *Journal of Cardiovascular Electrophysiology* 14(4):422-430.

D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.

Demaria, A.N. et al. (Dec. 17, 2003). "Highlights of the Year JACC 2003," *Journal of the American College of Cardiology* 42(12):2156-2166.

Deneu, S. et al. (Jul. 11, 1999). "Catheter Entrapment by Atrial Suture During Minimally Invasive Port-access Cardiac Surgery," *Canadian Journal of Anesthesia* 46(10):983-986.

Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.

Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.

Donnino, R. et al. (2007). "Left Atrial Appendage Thrombus Outside of a 'Successful' Ligation," *European Journal of Echocardiography* pp. 1-2.

Feinberg, W.M. et al. (Mar. 13, 1995). "Prevalence, Age Distribution, and Gender of Patients With Atrial Fibrillation," *Arch Intern Med* 155:469-473.

Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.

Final Office Action mailed on Apr. 14, 2010, for U.S. Appl. No. 11/600,671, filed Nov. 15, 2006, 7 pages.

Fisher, D.C. et al. (Dec. 1998). "Large Gradient Across a Partially Ligated Left Atrial Appendage," *Journal of the American Society of Echocardiography* 11(12):1163-1165.

Friberg, L. et al. (2006). "Stroke Prophylaxis in Atrial Fibrillation: Who Gets it and Who Does Not?" *European Heart Journal* 27:1954-1964.

Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.

Fuster, V. et al. (Oct. 2001). "ACC/AHA/ESC Guidelines for the Management of Patients with Atrial Fibrillation," *European Heart Journal* 22(20):1852-1923.

Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.

Gardiner, G.A. Jr. et al. (Apr. 1986). "Complications of Transluminal Angioplasty," *Radiology* 159:201-208.

Gillinov, A.M. (2007). "Advances in Surgical Treatment of Atrial Fibrillation," *Stroke* 38(part 2):618-623.

Gilman, R.A. et al. (Apr. 1963). "Direct Left Ventricular Puncture," *California Medicine* 98(4):200-203.

Goodwin, W.E. et al. (Nov. 1950). "Translumbar Aortic Puncture and Retrograde Catheterization of the Aorta in Aortography and Renal Arteriography," *Annals of Surgery* 132(5):944-958.

Gottlieb, L.K. et al. (Sep. 12, 1994). "Anticoagulation in Atrial Fibrillation," *Arch Intern Med.* 154:1945-1953.

Graffigna, A. et al. (1993). "Surgical Treatment of Wolff-Parkinson-White Syndrome: Epicardial Approach Without the Use of Cardiopulmonary Bypass," *J. Card. Surg.* 8:108-116.

Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.

Halperin, J.L. et al. (Aug. 1988). "Atrial Fibrillation and Stroke: New Ideas, Persisting Dilemmas," *Journal of the American Heart Association* 19(8):937-941.

Halperin, J.L. et al. (Oct. 1, 2003). "Obliteration of the Left Atrial Appendage for Prevention of Thromboembolism," *Journal of the American College of Cardiology* 42(7):1259-1261.

Hammill, S.C. (May 2006). "Epicardial Ablation: Reducing the Risks," *J. Cardiovasc. Electrophysiol.* 17:550-552.

Hara, H. et al. (Jan. 2008). "Percutaneous Left Atrial Appendage Obliteration," *JACC: Cardiovascular Imagin* 1(1):92-93.

Hart, R.G. et al. (Nov. 2, 1999). "Atrial Fibrillation and Thromboembolism: A Decade of Progress in Stroke Prevention," *Annals of Internal Medicine* 131(9):688-695.

Hart, R.G. et al. (2001). "Atrial Fibrillation and Stroke: Concepts and Controversies," *Stroke* 32:803-808.

Hart, R.G. (Sep. 11, 2003). "Atrial Fibrillation and Stroke Prevention," *The New England Journal of Medicine* 349(11):1015-1016.

Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at The Canadian Cardiovascular Congress 2003, Toronot, Canada, Abstract No. 666, 2 pages.

Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.

Hein, R. et al. (2005). "Patent Foramen Ovale and Left Atrial Appendage: New Devices and Methods for Closure," *Pediatric Cardiology* 26(3):234-240.

Heist, E.K. et al. (Nov. 2006). "Analysis of the Left Atrial Appendage by Magnetic Resonance Angiography in Patients with Atrial Fibrillation," *Heart Rhythm* 3(11):1313-1318.

Ho, I. et al. (Apr. 24, 2007). "Percutaneous Epicardial Mapping Ablation of a Posteroseptal Accessory Pathway," *Circulation* 115:e418-e421.

Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.

Hoit, B.D. et al. (Jan. 1993). "Altered Left Atrial Compliance After Atrial Appendectomy. Influence on Left Atrial and Ventricular Filling," *Circulation Research* 72(1):167-175.

Inoue, Y. et al. (Jul.-Aug. 1997). "Video Assisted Thoracoscopic and Cardioscopic Radiofrequency Maze Ablation," *Asaio Journal* 43(4):334-337, Abstract Only.

Jaïs, P. et al. (2003). "Radiofrequency Ablation for Atrial Fibrillation," *European Society of Cardiology* 5(Supplement H):H34-H39.

Jongbloed, M.R.M. et al. (2005). "Clinical Applications of Intracardiac Echocardiography in Interventional Procedures," *Heart* 91:981-990.

Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.

Kanderian, A.S. et al. (2008). "Success of Surgical Left Atrial Appendage Closure: Assessment by Transesophageal Echocardiography," *Journal of the American College of Cardiology* 52(11):924-929.

Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.

Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.

Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.

Kerut, E.K. et al. (Jul. 2008). "Anatomy of the Left Atrial Appendage," *Echocardiography* 25(6):669-673.

Khargi, K. et al. (2005). "Surgical Treatment of Atrial Fibrillation: A Systematic Review," *European Journal of Cardiothoracic Surgery* 27:258-265.

Kistler, P.M. et al. (May 2007). "The Left Atrial Appendage: Not Just an Innocent Bystander," *J. Cardiovasc Electrophysiol* 18(5):465-466.

Klein, H. et al. (Apr. 1990). "The Implantable Automatic Cardioverter-Defibrillator," *Herz* 15(2):111-125, Abstract Only.

Kolb, C. et al. (Feb. 2004). "Incidence of Antitachycardia Therapy Suspension Due to Magnet Reversion in Implantable Cardioverter Defibrillators," *Pace* 27:221-223.

Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.

Lacomis, J.M. et al. (2007, e-pub. Oct. 17, 2007). "Dynamic Multidimensional Imaging of the Human Left Atrial Appendage," *Europace* 9:1134-1140.

Lee, R. et al. (1999). "The Closed Heart Maze: A Nonbypass Surgical Technique," *The Annals of Thoracic Surgery* 67:1696-1702.

Levinson, M.L. et al. (1998). "Minimally Invasive Atrial Septal Defect Closure Using the Subxyphoid Approach," *Heart Surg. Forum* 1(1):49-53, Abstract Only.

Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.

Li, H. (2007). "Magnet Decoration, Beautiful But Potentially Dangerous for Patients with Implantable Pacemakers or Defibrillators," *Heart Rhythm* 4(1):5-6.

Lindsay, B.D. (1996). "Obliteration of the Left Atrial Appendage: A Concept Worth Testing," *The Annals of Thoracic Surgery* 61:515.

Lip, G.Y.H. et al. (Jun. 2001). "Thromboprophylaxis for Atrial Flutter," *European Heart Journal* 22(12):984-987.

Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.

Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I)1-I7-I-22.

Mannam, A.P. et al. (Apr. 1, 2002). "Safety of Subxyphoid Pericardial Access Using a Blunt-Tip Needle," *The American Journal of Cardiology* 89:891-893.

Mattox, K.L. et al. (May 1997). "Newer Diagnostic Measure and Emergency Management," *Ches Surg Clin N Am.* 7(2):213-226, Abstract Only.

McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.

McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.

McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.

Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.

Miller, P.S.J. et al. (Feb. 2005). "Are Cost Benefits of Anticoagulation for Stroke Prevention in Atrial Fibrillation Underestimated?" *Stroke* 36:360-366.

Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.

Mráz, T. et al. (Apr. 2007). "Role of Echocardiography in Percutaneous Occlusion of the left Atrial Appendage," *Echocardiography* 24(4):401-404.

Nakai, T. et al. (May 7, 2002). "Percutaneous Left Atrial Appendage Occlusion (PLAATO) for Preventing Cardioembolism: First Experience in Canine Model," *Circulation* 105:2217-2222.

Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.

O'Donnell, M. et al. (2005). "Emerging Therapies for Stroke Prevention in Atrial Fibrillation," *European Heart Journal* 7(Supplement C):C19-C27.

Omran, H. et al. (1997). "Left Atrial Appendage Function in Patients with Atrial Flutter," *Heart* 78:250-254.

Onalan, O. et al. (2005). "Nonpharmacologic Stroke Prevention in Atrial Fibrillation," *Expert Rev. Cardiovasc. Ther.* 3(4):619-633.

Onalan, O. et al. (2007). "Left Atrial Appendage Exclusion for Stroke Prevention in Patients With Nonrheumatic Atrial Fibrillation," *Stroke* 38(part 2):624-630.

Ostermayer, S. et al. (2003). "Percutaneous Closure of the Left Atrial Appendage," *Journal of Interventional Cardiology* 16(6):553-556.

Ota, T. et al. (2006). "Epicardial Atrial Ablation Using a Novel Articulated Robotic Medical Probe Via a Percutaneous Subxiphoid Approach," *National Institute of Health* 1(6):335-340.

Ota, T. et al. (Oct. 2007). "Impact of Beating Heart Left Atrial Ablation on Left-sided Heart Mechanics," *The Journal of Thoracic and Cardiovascular Surgery* 134:982-988.

Pennec, P-Y. et al. (2003). "Assessment of Different Procedures for Surgical Left Atrial Appendage Exclusion," *The Annals of Thoracic Surgery* 76:2167-2168.

Perk, G. et al. (Aug. 2009). "Use of Real Time Three-Dimensional Transesophageal Echocardiography in Intracardiac Catheter Based Interventions," *J. Am Soc Echocardiogr* 22(8):865-882.

Pollick C. (Feb. 2000). "Left Atrial Appendage Myopathy," *Chest* 117(2):297-308.

Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.

Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.

Robicsek, F. (1987). "Closed-Chest Decannulation of Transthoracically Inserted Aortic Balloon Catheter without Grafting," *Journal of Cardiac Surgery* 2(2):327-329.

Ross, J. Jr. et al. (Jun. 3, 2008). "Transseptal Left Heart Catheterization: A 50-Year Odyssey," *Journal of the American College of Cardiology* 51(22):2107-2115.

Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.

Ruchat, P. et al. (2002). "Off-pump Epicardial Compartmentalization for Ablation of Atrial Fibrillation," *Interactive Cardio Vascular and Thoracic Surgery* 1:55-57.

Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.

Sapp, J. et al. (Dec. 2001). "Electrophysiology and Anatomic Characterization of an Epicardial Accessory Pathway," *Journal of Cardiovascular Electrophysiology* 12(12):1411-1414.

Scharf, C. et al. (2005). "Catheter Ablation for Atrial Fibrillation: Pathophysiology, Techniques, Results and Current Indications," *Continuous Medical Education* 8:53-61.

Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

Schneider, B. et al. (2005, e-pub. Aug. 22, 2005). "Surgical Closure of the Left Atrial Appendage—A Beneficial Procedure?" *Cardiology* 104:127-132.

Schweikert, R.A. et al. (Sep. 16, 2003). "Percutaneous Pericardial Instrumentation for Endo-Epicardial Mapping of Previously Failed Ablation," *Circulation* 108:1329-1335.

Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.

Sengupta, P.P. et al. (2005). "Transoesophageal Echocardiography," *Heart* 91:541-547.

Sharada, K. et al. (2005). "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (Jul. 15, 2002). "Gaining Access to the Pericardial Space," *The American Journal of Cardiology* 90:203-204.

Sosa, E. et al. (Apr. 2005). "Epicardial Mapping and Ablation Techniques to Control Centricular Tachycardia," *Journal of Cardiovasc. Electrphsiol.* 16(4):449-452.

Sparks, P.B. et al. (2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.

Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.

Stöllberger, C. et al. (2000). "Is the Left Atrial Appendage Our Most Lethal Attachment?" *European Journal of Cardio-Thoracic Surgery* 18:625-626.

Stöllberger, C. et al. (Dec. 2003). "Elimination of the Left Atrial Appendage to Prevent Stroke or Embolism?: Anatomic, Physiologic, and Pathophysiologic Considerations," 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.

Stöllberger, C. et al. (2007). "Arguments Against Left Atrial Appendage Occlusion for Stroke Prevention," *Stroke* 38:e77.

Stöllberger, C. et al. (2007). "Leave the Left Atrial Appendage Untouched for Stroke Prevention!" *Journal of Thoracic and Cardiovascular Surgery* 134(2):549-550.

Su, P. et al. (Sep. 2008, e-pub. May 8, 2007). "Occluding the Left Atrial Appendage: Anatomical Considerations," *Heart* 94(9):1166-1170.

Subramanian, V.A. (Jun. 1997). "Less Invasive Arterial CABG on a Beating Heart," *Ann. Thorac. Surg.* 63(6 Suppl.):S68-S71.

Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.

Sun, F. et al. (Feb. 2006). "Subxiphoid Access to Normal Pericardium with Micropuncture Set: Technical Feasibility Study in Pigs," *Radiology* 238(2):719-724.

Szili-Torok, T. et al. (2001). "Transseptal Left Heart Catheterisation Guided by Intracardiac Echocardiography," *Heart* 86:e11-e15.

Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.

Tomar, M. et al. (Jul.-Aug. 2006). "Transcatheter Closure of Fossa Ovalis Atrial Septal Defect: A Single Institutional Experience," *Indian Heart Journal* 58(4):325-329.

Troughton, R.W. et al. (Feb. 28, 2004). "Pericarditis," *The Lancet* 363:717-727.

Ulicny K.S. et al. (Jun. 1992). "Conjoined Subrectus Pocket for Permanent Pacemaker Placement in the Neonate," *Ann Thorac Surg.* 53(6):1130-1131, Abstract Only.

Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.

Von Korn, H. et al. (2006). "Simultaneous Combined Interventional Percutaneous Left Atrial Auricle and Atrial Septal Defect Closure," *Heart* 92:1462.

Wang, T.J. et al. (Aug. 27, 2003). "A Risk Score for Predicting Stroke or Death in Individuals With New-Onset Atrial Fibrillation in the Community," *American Medical Association* 290(8):1049-1056.

W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.

Wolber, T. et al. (Jan. 2007). "Potential Interference of Small Neodymium Magnets with Cardiac pacemakers and Implantable Cardioverter-defibrillators," *Heart Rhythm* 4(1):1-4.

Wolf, P.A. et al. (Oct. 1978). "Epidemiologic Assessment of Chronic Atrial Fibrillation and Risk of Stroke: The Fiamingham Study," *Neurology* 28:973-977.

Wolf, P.A. et al. (Aug. 1991). "Atrial Fibrillation as an Independent Risk Factor for Stroke: The Framingham Study," *Stroke* 22(8):983-988.

Wolf, P.A. et al. (Feb. 9, 1998). "Impact of Atrial Fibrillation on Mortality, Stroke, and Medical Costs," *Arch Intern Med* 158:229-234.

Wong, J.W.W. et al. (2006). "Impact of Maze and Concomitant Mitral Valve Surgery on Clinical Outcomes," *The Annals of Thoracic Surgery* 82:1938-1947.

Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.

Wood, M.A. (Jan. 2006). "Percutaneous Pericardial Instrumentation in the Electrophysiology Laboratory: A Case of Need," *Heart Rhythm* 3(1):11-12.

Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.

Wyse, D.G. et al. (Dec. 5, 2002). "Of 'Left Atrial Appendage Amputation, Ligation, or Occlusion in Patients with Atrial Fibrillation'," *N Engl J Med* 347(23):1825-1833, Abstract Only.

Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.

Zapolanski, A. et al. (May 2008). "Safe and Complete Exclusion of the left Atrial Appendage, A Simple Epicardial Approach," *Innovations* 3(3):161-163.

Zenati, M.A. et al. (Sep. 2003). "Left Heart Pacing Lead Implantation Using Subxiphoid Videopericardioscopy," *Journal of Cariodvascular Electrophysiology* 14(9):949-953.

Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.

Zenati, M.A. et al. (2005). "Modification of the Left Atrial Appendage," Chapter 12 in *Innovative Mangement of Atrial Fibrillation*, Schwartzman, David ed., Blackwell Science Ltd., 5 pages.

Blackshear, J.L. et al. (2003). "Thorascopic Extracardiac Obliteration of the Left Atrial Appendage for Stroke Risk Reduction in Atrial Fibrillation," *J. Am. Coll. Cardiol.* 42:1249-1252.

Cox, J.L. et al. (1991). "The Surgical Treatment of Atrial Fibrillation IV. Surgical Technique," *J. Thorac. Cardiovasc. Surg.* 101(4):584-592.

Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.

Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.

Cox, J.L. et al. (Nov. 1999). "Impact of the Maze Procedure on the Stroke Rate in Patients with Atrial Fibrillation," *J. Thorac. Cardiovasc. Surg.* 118:833-840.

Dullum, M.K.C. et al. (1999). "Xyphoid MIDCAB: Report of the Technique and Experience with a Less Invasive MIDCAB Procedure," *Heart Surgery Forum* 2(1):77-81.

Kim, K.B. et al. (Jan. 1998). "Effect of the Cox Maze Procedure on the Secretion of Atrial Natriuretic Peptide," *J. Thorac. Cardiovasc. Surf.* 115(1):139-46; discussion 146-147.

Macris, M. et al. (Jan. 1999). "Minimally Invasive Access of the Normal of the Normal Pericardium: Initial Clinical Experience with a Novel Device," *Clin. Cardiol.* 22(Suppl. I):I-36-I-39.

Morris, J.J. Jr. (1997). "Transvenous Versus Transthoracic Cardiac Pacing," Chapter 16 in *Cardiac Pacing* pp. 239-245.

Naclerio, et al. (1997). "Surgical Techniques for Permanent Ventricular Pacing," Chapter 10 in *Cardiac Pacing* pp. 145-168.

Odell, J.A. et al. (1996). "Thorascopic Obliteration of the Left Atrial Appendage: Potential for Stroke Reduction?" *Ann. Thorac. Surg.* 61:565-569.

Seferovic, P. et al. (Jan. 1999). "Initial Clinical Experience with the Perducer Device: Promising New Tool in the Diagnosis and Treatment of Pericardial Disease," Clin. Cardiol. 22(Supp I.):1-30-1-35.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Stewart, S. (1974). "Placement of the Sutureless Epicardial Pacemaker Lead by the Subxiphoid Approach," *Ann. Of Thoracic Surg.* 18(3):308-131.

Stokes, K. (Jun. 1990). "Implantable Pacing Lead Technology," *IEEE Engineering in Medicine and Biology* pp. 43-49.

Suehiro, S. et al. (1996). "Echocardiography-Guided Pericardiocentesis With a Needle Attached to a Probe," *Ann. Thoracic Surg.* 61:741-742.

Watkins, L. et al. (Nov. 1982). "Implantation of the Automatic Defibrillator: The Subxiphoid Approach," *Ann. of Thoracic Surg.* 34(5):514-520.

Final Office Action mailed on Jul. 21, 2010, for U.S. Appl. No. 11/400,714, filed Apr. 7, 2006, 10 pages.

Final Office Action mailed on Apr. 26, 2011, for U.S. Appl. No. 12/037,802, filed Feb. 26, 2008, 9 pages.

Final Office Action mailed on Oct. 28, 2011, for U.S. Appl. No. 12/055,213, filed Mar. 25, 2008, 15 pages.

International Preliminary Report on Patentability mailed on Aug. 12, 2010, for PCT Application No. PCT/US2008/076703, filed on Sep. 17, 2008, 10 pages.
International Search Report mailed on Jul. 30, 2010, for PCT Application No. PCT/US2008/076703, filed on Sep. 17, 2008, 2 pages.
Non-Final Office Action mailed on Dec. 30, 2009, for U.S. Appl. No. 11/400,714, filed Apr. 7, 2006, 8 pages.
Non-Final Office Action mailed on Jul. 22, 2010, for U.S. Appl. No. 12/037,802, filed Feb. 26, 2008, 10 pages.
Non-Final Office Action mailed on Nov. 15, 2010, for U.S. Appl. No. 12/055,213, filed Mar. 25, 2008, 18 pages.
Non-Final Office Action mailed on Apr. 28, 2011, for U.S. Appl. No. 12/055,213, filed Mar. 25, 2008, 20 pages.
Non-Final Office Action mailed on Oct. 27, 2011, for U.S. Appl. No. 12/363,359, filed Jan. 30, 2009, 11 pages.
Non-Final Office Action mailed on Nov. 9, 2011, for U.S. Appl. No. 12/363,381, filed Jan. 30, 2009, 10 pages.
Non-Final Office Action mailed on Dec. 22, 2011, for U.S. Appl. No. 13/033,532, filed Feb. 23, 2011, 8 pages.
Notice of Allowance mailed on Sep. 17, 2010, for U.S. Appl. No. 10/963,371, filed Oct. 11, 2004, 7 pages.
Notice of Allowance mailed on Sep. 17, 2010, for U.S. Appl. No. 11/600,671, filed Nov. 15, 2006, 7 pages.
Notice of Allowance mailed on Nov. 24, 2010, for U.S. Appl. No. 11/400,714, filed Apr. 7, 2006, 8 pages.
Written Opinion of the International Searching Authority mailed on Jul. 30, 2010, for PCT Application No. PCT/US2008/076703, filed on Sep. 17, 2008, 8 pages.

* cited by examiner

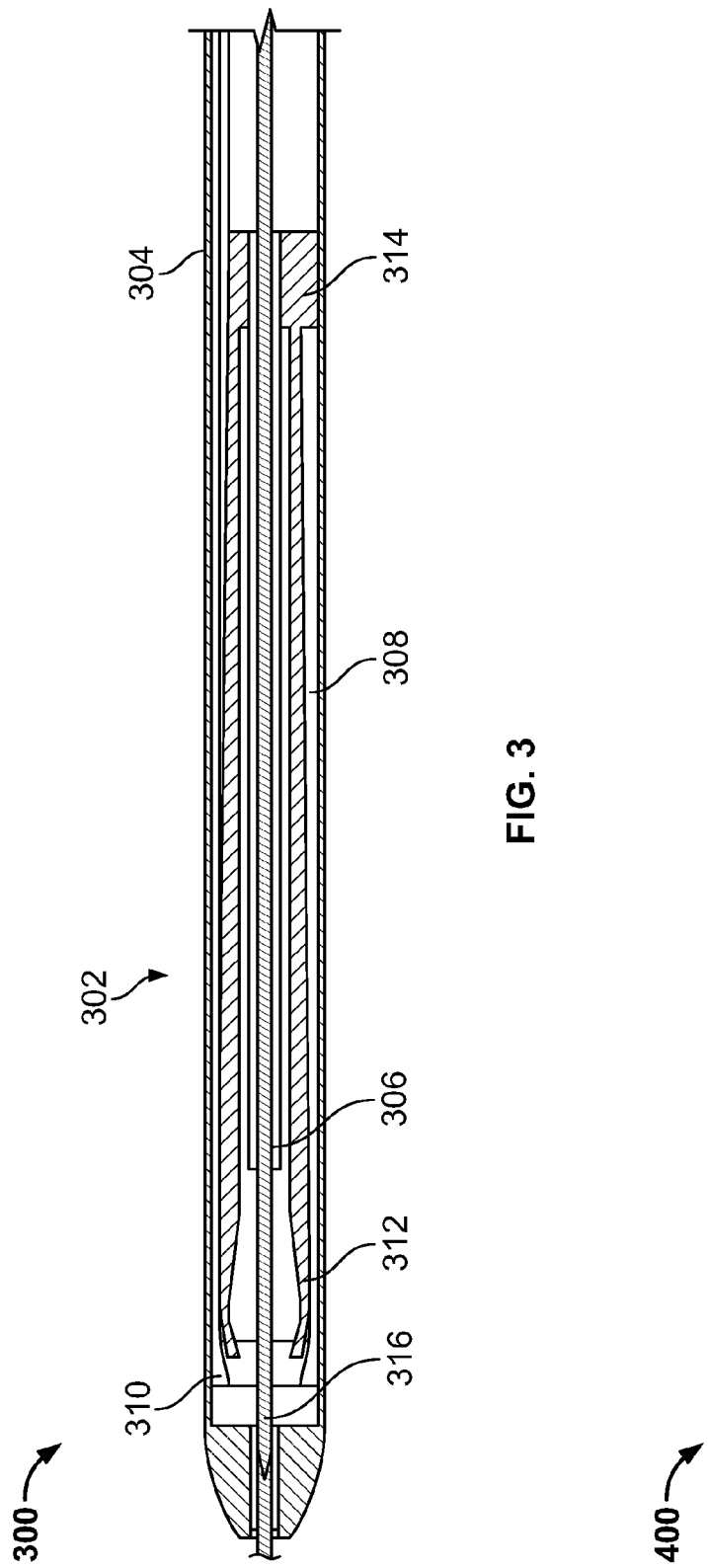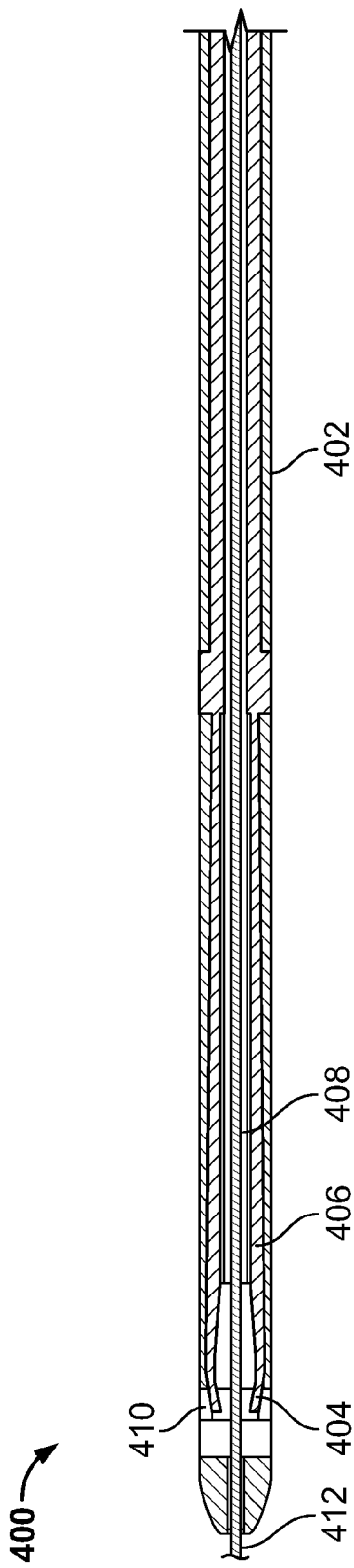

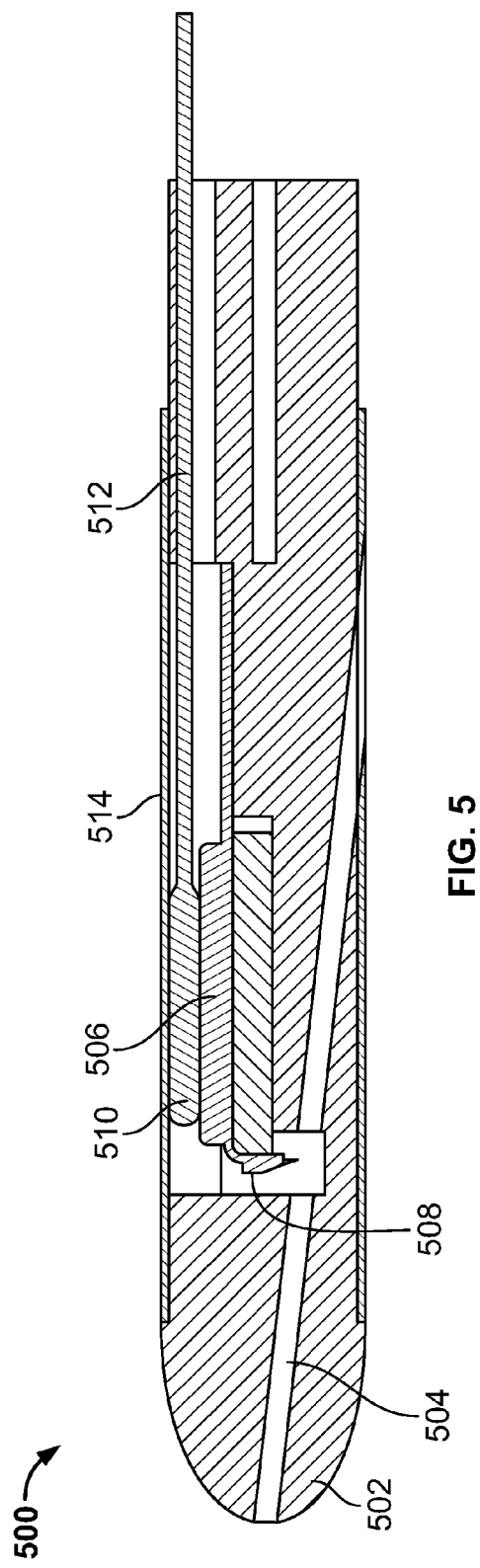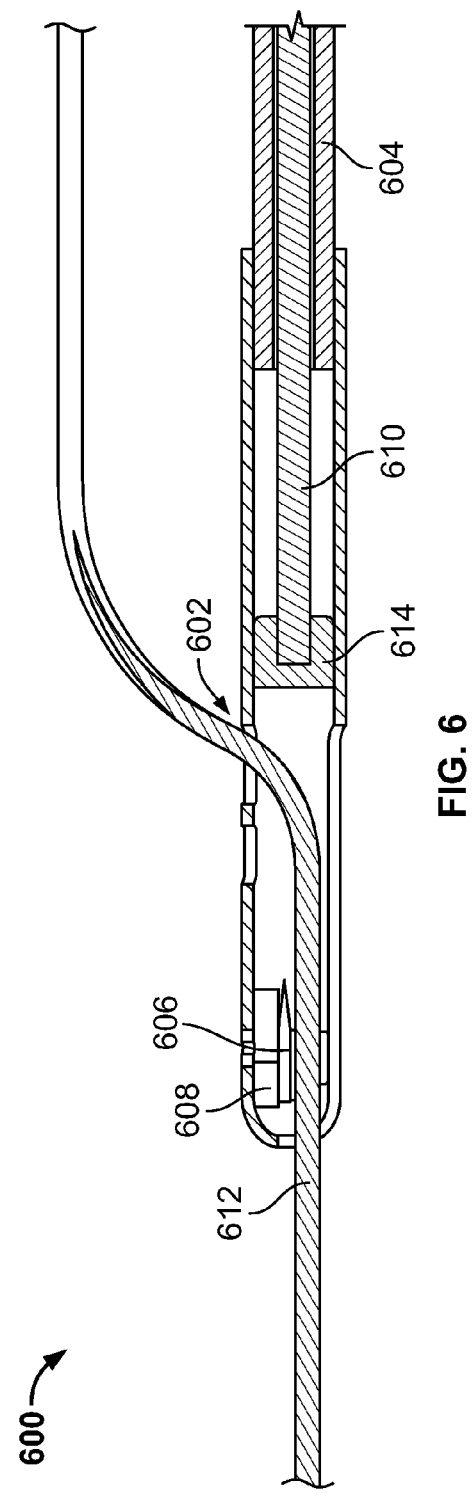

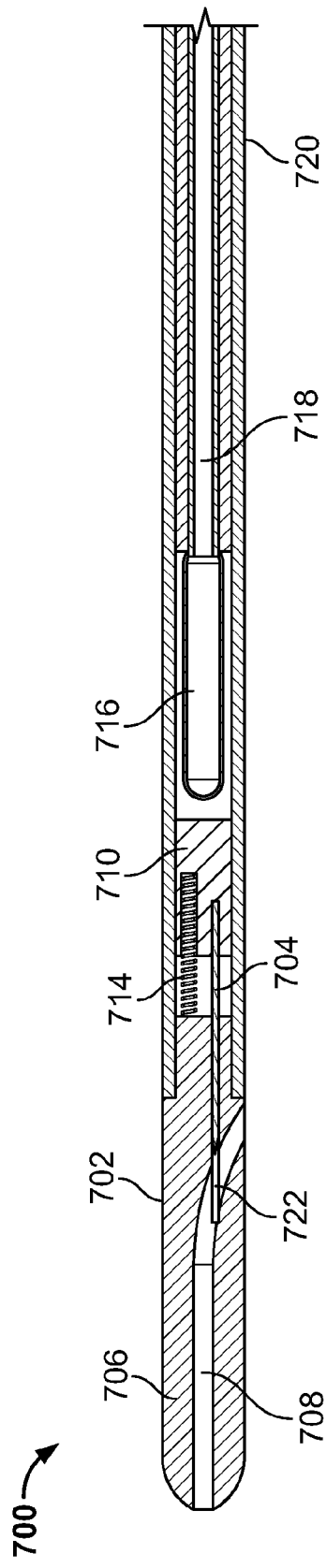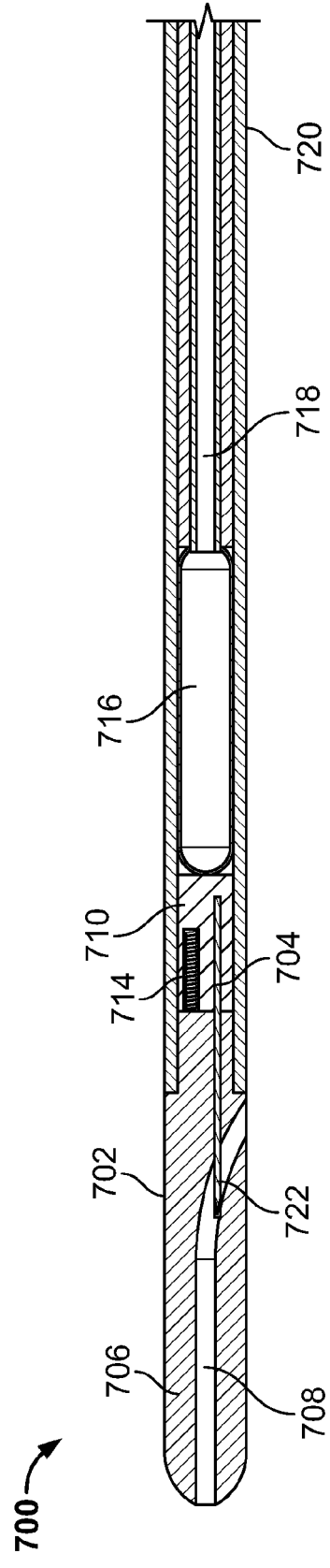

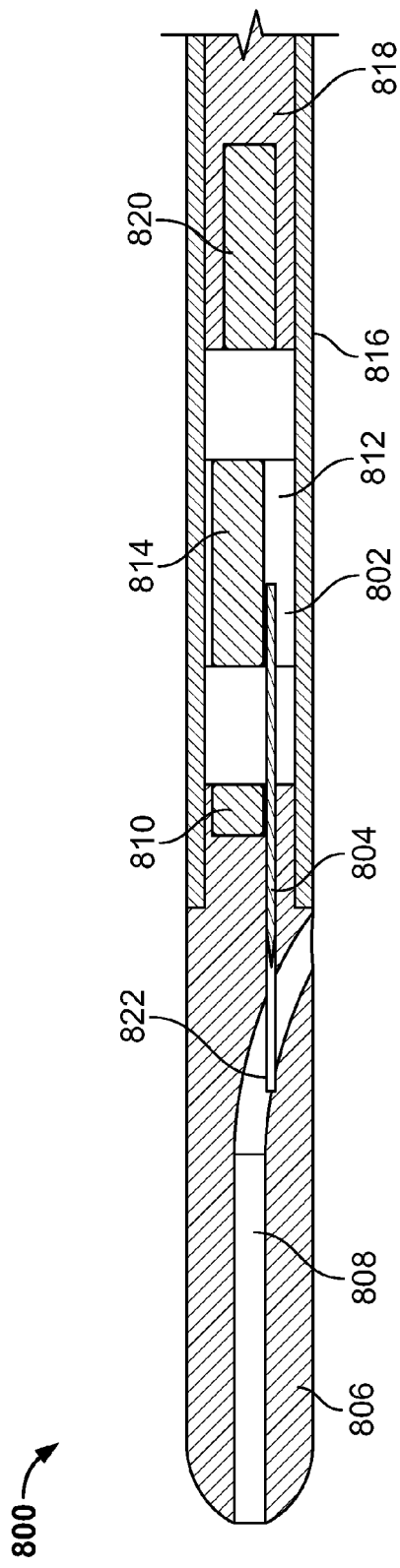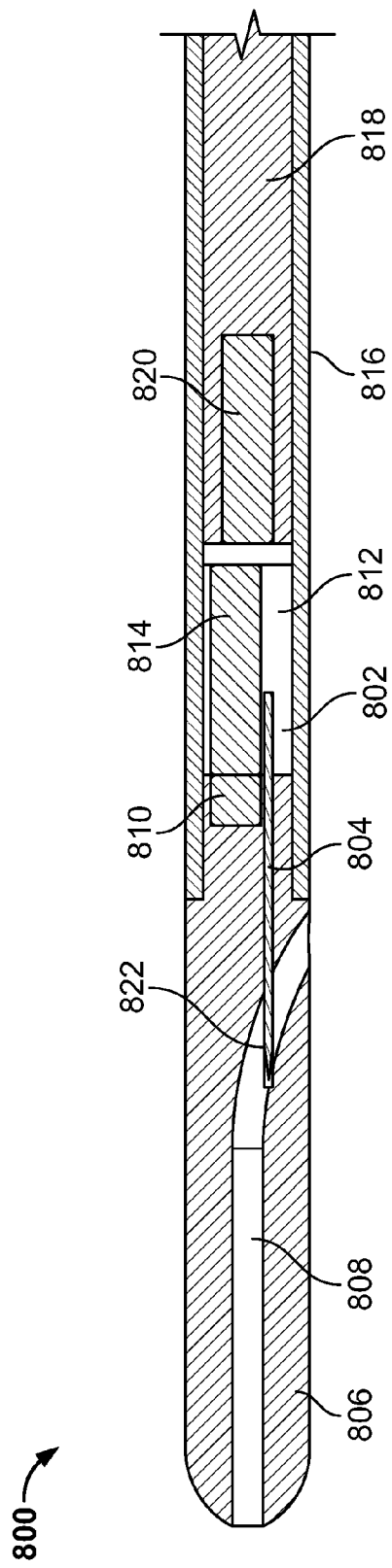
FIG. 8A
FIG. 8B

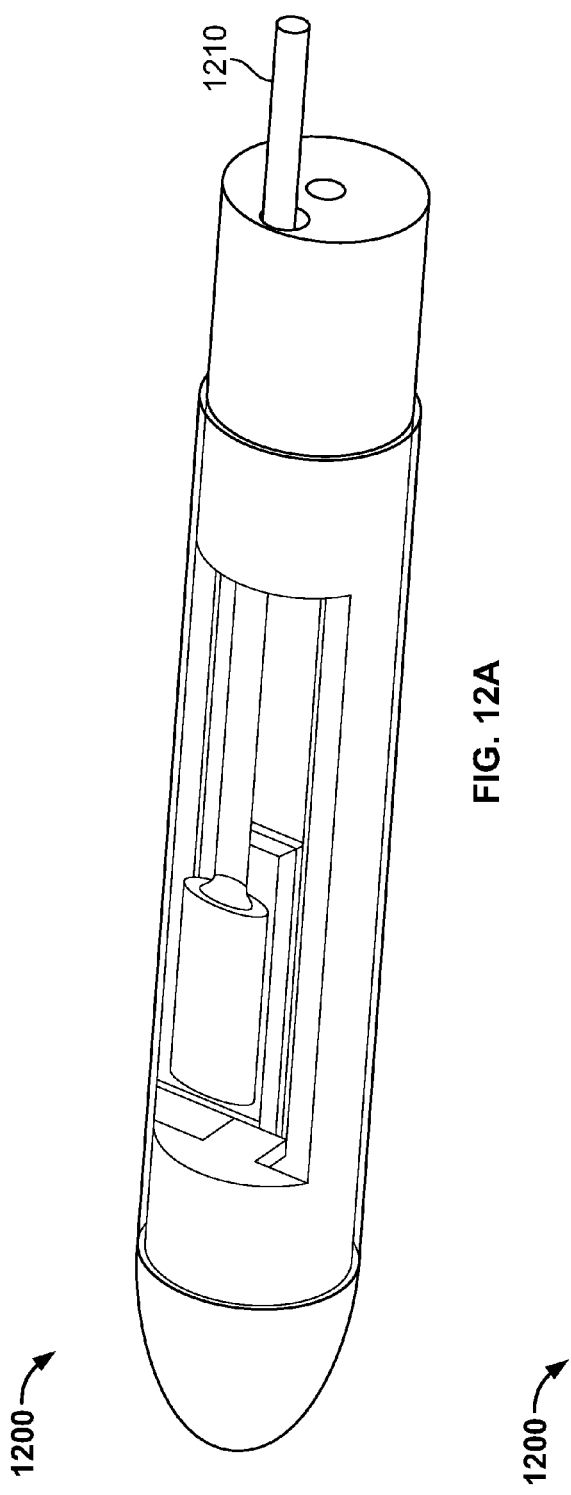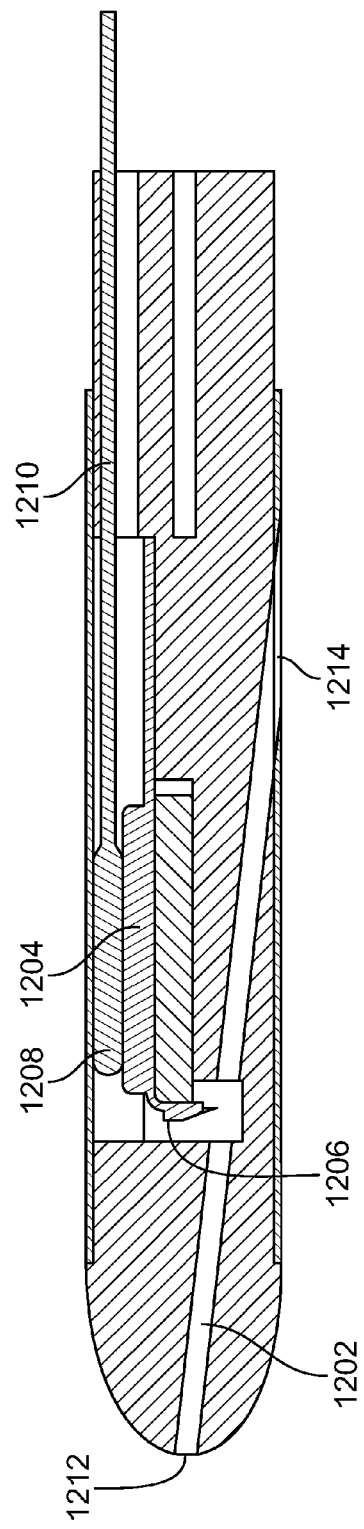

DEVICES AND METHODS FOR REMOTE SUTURE MANAGEMENT

CROSS-REFERENCE TO RELATED APPLICATIONS

This application claims priority to U.S. Provisional Patent Application Ser. No. 60/974,051 filed on Sep. 20, 2007, which is hereby incorporated by reference in its entirety.

FIELD

In general, the devices and methods described herein relate to the manipulation and management of sutures or suture-like materials. In particular, the devices and methods described herein relate to remotely manipulating and managing sutures or suture-like materials.

BACKGROUND

The use of sutures has been widespread in surgical procedures. Sutures may be used to close incisions or wounds, to join tissue segments, or ligate sections of tissue. After a suture has been put to its intended use, it is often tied into a knot to secure it in place. When the suture is placed in a region having restricted access, tying a knot may be particularly difficult. Thus, knots are often formed outside of a patient and pushed toward the region. Once the knot has been positioned in the region, the ends of the suture generally need to be trimmed back, which may be difficult using standard instruments. As such, additional devices and methods for remotely manipulating a suture or suture-like material may be desirable.

BRIEF SUMMARY

Described here are devices and methods for suture management. In some variations, the devices comprise an elongate tubular member having a proximal end, a distal end, a lumen therebetween, a cantilever blade positioned near the distal end of the elongate tubular member, and an expandable member positioned adjacent the cantilever blade for actuating the cantilever blade. The lumen is configured for the passage of a suture at least partially therethrough. The expandable member may be any suitable expandable member. In some variations, the expandable member is inflatable (e.g., a balloon). In other variations, the expandable member comprises a pair of jaws. In still other variations, the device may include one or more retractable guides that may help to bring the suture into a position where it may be severed by the cantilever blade. In some variations, the retractable guide may comprise a guide loop. In other variations, the retractable guide may comprise a spiral loop.

Other devices for severing a suture are also described. For example, devices are also described comprising an elongate tubular member having a proximal end, a distal end, and a lumen therebetween, opposed cutting blades near the distal end, and an actuator for actuating the opposed cutting blades, where the actuator is disposed at least in part about the outer surface of the cutting blades. The actuator may be any suitable structure. In some variations, the actuator comprises an expandable member. In some of these variations, the actuator may be inflatable. In some of these variations, the actuator may be a balloon. In other variations, the actuator comprises actuation jaws configured to actuate the opposed blades when pulled proximally or pushed distally. In still other variations, the device may comprise a retractable guide as described above.

Additional devices are also described. For example, devices are described comprising an elongate tubular member having a proximal end, a distal end, and a lumen at least partially therebetween, the elongate tubular member comprising an aperture in a wall thereof for passage of a suture therethrough, and a blade connected to a blade housing and disposed within the lumen, where the blade is oriented parallel to the longitudinal axis of the lumen, and the blade and blade housing are slidable within the lumen. In some of these variations, the device further comprises an actuator configured to actuate the slidable blade. In some of these variations, the actuator may be an expandable member. In other variations, the actuator may be a pull wire. In still other variations, the actuator may include one or more magnets. In other variations, the actuator may include a plunger. Some variations of the devices described here further comprise a handle. In some of these variations, the handle comprises one or more safety features. The devices may include one or more retractable guides as described above.

Other described devices comprise a first elongate tubular member comprising a proximal end, a distal end, and a lumen at least partially therebetween, the first elongate tubular member having a substantially closed distal end having an aperture therein, the aperture having at least one cutting edge, and a second elongate tubular member comprising a proximal end, a distal end, and a lumen at least partially therebetween, the second elongate tubular member having a substantially closed distal end having an aperture therein, the aperture having at least one cutting edge. The first and second elongate tubular members are rotatable relative to one another such that upon rotation, the cutting edge of the first elongate tubular member and the cutting edge of the second elongate tubular member are brought toward one another. In some variations, the device comprises one or more retractable guides as described above.

Also described here are methods for severing a suture. In some variations, the methods comprise advancing a cutting assembly over a suture, the cutting assembly comprising a first elongate tubular member comprising a proximal end, a distal end, and a lumen at least partially therebetween, the first elongate tubular member having a substantially closed distal end having an aperture therein, the aperture having at least one cutting edge and a second elongate tubular member comprising a proximal end, a distal end, and a lumen at least partially therebetween, the second elongate tubular member having a substantially closed distal end, having an aperture therein, the aperture having at least one cutting edge, the suture passing through the distal end of the cutting assembly when the apertures of the first and second elongate tubular members are aligned, and rotating the first elongate tubular member with respect to the second elongate tubular member. Rotation of the first elongate tubular member with respect to the second elongate tubular member causes the cutting edges of the first and second elongate tubular members to be brought toward one another.

In other variations, the methods comprise retracting a blade assembly within an elongate tubular member to contact and sever a suture, the elongate tubular member comprising a proximal end, a distal end, and a lumen at least partially therethrough, the blade assembly comprising a blade and a blade housing, the blade assembly being slidably disposed within the lumen of the elongate tubular member, and wherein the blade is oriented parallel to the longitudinal axis of the lumen. In some of these variations, retracting the blade assembly comprises retracting the blade assembly using one or more magnets. In other variations, retracting the blade assembly comprises retracting the blade assembly using a shaft slidably disposed within the tubular member.

BRIEF DESCRIPTION OF THE DRAWINGS

FIG. 3 is a cross-sectional side view of a suture management device having a cutting assembly with cutting jaws.

FIG. 4 is a cross-sectional side view of a suture management device having a cutting assembly with cutting jaws.

FIG. 5 is a cross-sectional side view of a suture management device having a cutting assembly with a cantilevered blade.

FIG. 6 is a cross-sectional side view of a suture management device having a cutting assembly with a longitudinally oriented blade.

FIGS. 7A and 7B are cross-sectional side views of a suture management device having a balloon-actuated cutting assembly.

FIGS. 8A and 8B are cross-sectional side views of a suture management device having a magnetically actuated cutting assembly.

FIG. 12A is a perspective view and FIG. 12B is a cross-sectional side view of a variation of a suture engagement portion.

DETAILED DESCRIPTION

Described here are devices and methods for managing and manipulating sutures remotely from a user. When reference is made to the term "suture" herein, it should be understood that the term suture is generic and is intended to capture a wide variety of sutures and suture-like materials, including materials such as filaments, yarns, threads, chords, strips, and any combination of the foregoing, and the like. In some variations, the devices described here may be used to push or guide a suture, with or without a surgical knot, to a remote location. In some of these variations, the devices may be used to sever a suture at a location remote from the user. In some of these variations, the devices may be used to sever a suture at a predetermined or measured distance from a knot. Additionally, in some variations, the devices may be additionally configured to remove a knot or a knotted section of a tied suture. This may provide particular utility in instances where removing an undesirable suturing outcome is desirable.

Figure 1A:
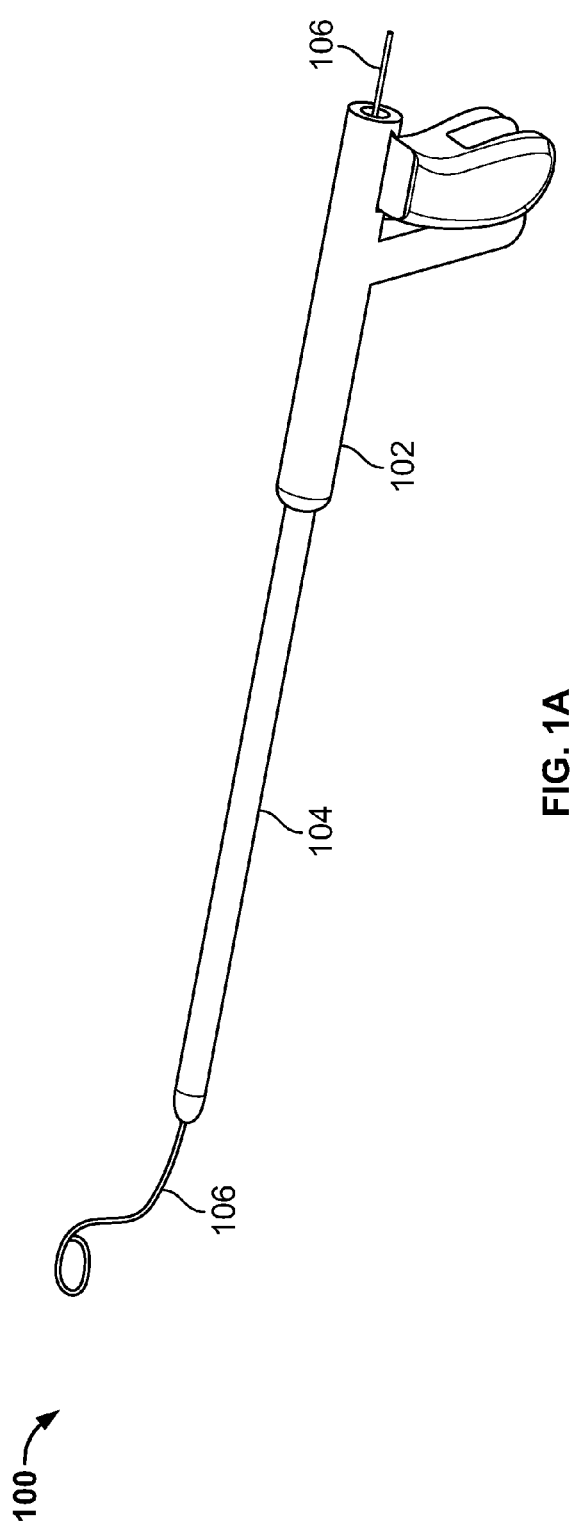
FIG. 1A is a perspective view of one variation of a suture management device.
Figure 1B:
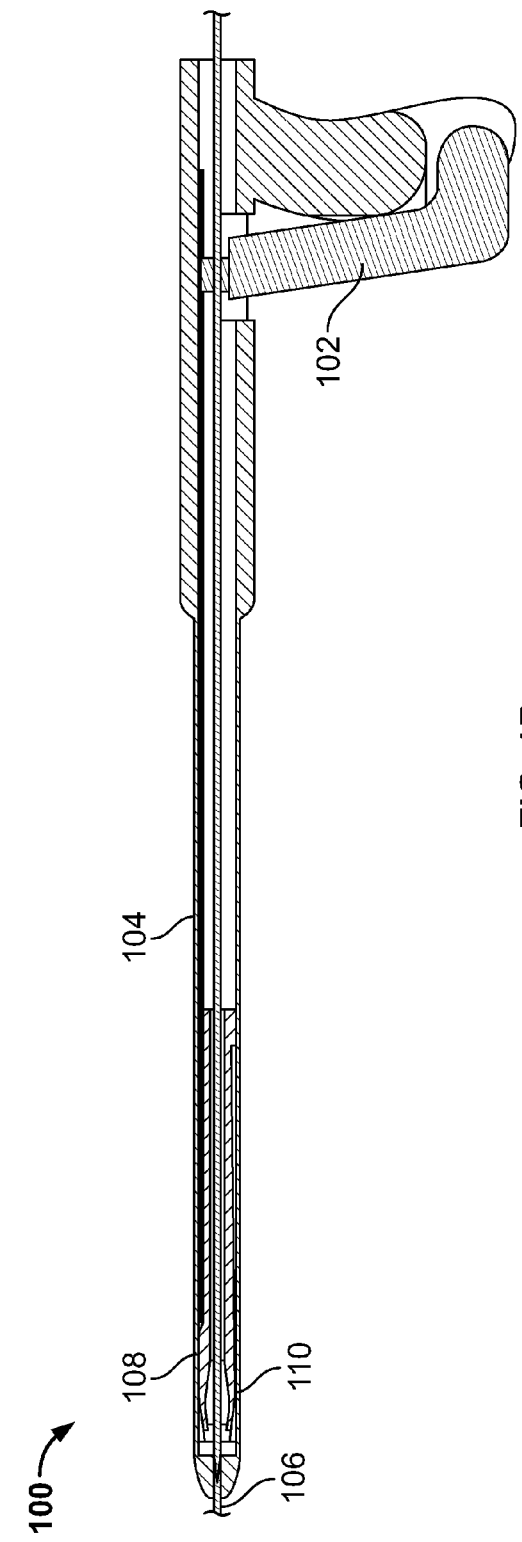
FIG. 1B is a cross-sectional side view of the same suture management device.
Figure 2:
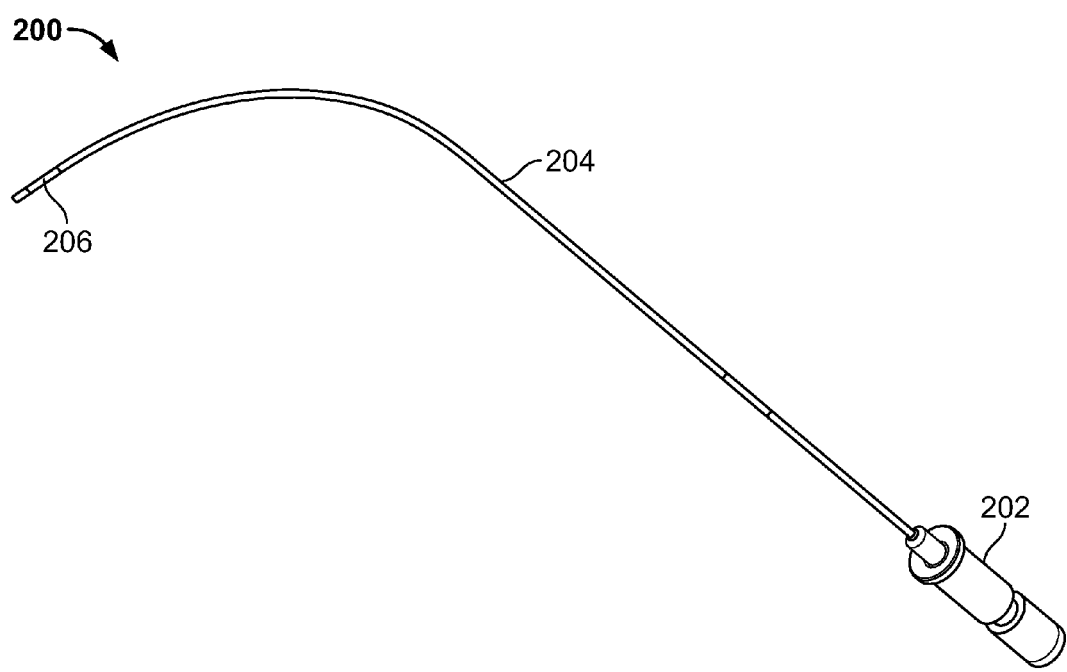
FIG. 2 is a perspective view of a variation of a suture management device.

Generally, the devices described here comprise a handpiece, a catheter body, and one or more cutting assemblies. FIGS. 1A and 1B show one such variation of suture management device (100). FIG. 1A shows a perspective view of suture management device (100), including handpiece (102) and catheter body (104). Also shown there is suture (106). FIG. 1B shows a cross-sectional side view of suture management device (100), further showing cutting assembly (108) including cutter jaws (110) held within catheter body (104). While shown in FIG. 1B as having cutter jaws (110), cutting assembly (108) may have any configuration of elements, as will be described in more detail below. In some variations, the device may further comprise a suture engagement portion. FIG. 2 shows one such variation of suture management device (200). Shown there is handpiece (202), catheter section (204), and suture engagement portion (206). Suture engagement portion (206), which will be described in more detail below, generally engages at least a section of a suture (not shown) and may take on any suitable configuration. In other variations, the device may further comprise a retractable guide, which will be described in more detail below.

Catheter Section

In some variations, the suture management device comprises one or more catheter sections. A catheter section may be any structure capable of being advanced to a location remote from a user. For example, the catheter section may comprise a tube, sheath, or catheter body, which defines one or more lumens or channels. The catheter section may be made of any suitable material, may have any suitable geometry or configuration, and be made to have any suitable property. All or a portion of the catheter section may be flexible. Conversely, all or a portion of the catheter section may be rigid. Of course, the catheter section may be flexible along a portion of its length, and rigid along a portion of its length.

The catheter section may be guidable or steerable to a location remote from a user (e.g., using one or more pull or push wires, cables, or the like). Similarly, the catheter section may comprise or otherwise include one or more preshaped curves or bends along its length for facilitating positioning. The catheter section may also comprise one or more layers, coatings, or specialized surfaces. In some of these variations, at least a portion of the outer surface of the catheter section may be coated with, made from, or otherwise comprise a lubricious material such as PTFE. In others of these variations, the catheter section may comprise one or more coatings, reservoirs, or the like, which are configured to release one or more beneficial agents, such as, but not limited to antibiotics, antimicrobial agents, and anti-inflammatory agents.

Cutting Assemblies

The cutting assemblies described here may be used to sever a suture upon actuation of the suture management device. The cutting assembly may be contained entirely within a catheter section or a suture engagement portion, but need not be. In variations where the cutting assembly is entirely contained within the suture management device, the cutting assembly may be configured to come into contact only with suture. This, in turn, may prevent the cutting assembly from cutting or damaging bodily tissues. Additionally, the forces associated with operating the cutting assembly may be internalized within the suture management device, which may in turn prevent the cutting assembly from imparting a force to the suture management device. This may further prevent tissue trauma.

In some variations, the cutting assembly includes one or more cutter jaws. Indeed, FIG. 3 illustrates a cross-sectional view of the distal end of one such variation of suture management device (300). Shown there is cutting assembly (302) enclosed within catheter section (304). In this variation, cutting assembly (302) comprises suture channel (306), actuation cannula (308) attached to actuation jaws (310), and cutter jaws (312) attached to catheter section (304) via connection sleeve (314). Also shown there is suture (316). While shown in FIG. 3 as being disposed within catheter section (304), it should be appreciated that cutting assembly (302) may be located anywhere in or on suture management device (300), including, but not limited to, a handpiece (not shown) or a suture engagement portion (not shown). In the variation shown in FIG. 3, actuation cannula (308) and actuation jaws (310) may be slidably disposed within catheter section (304), and may be engagable with a handpiece (not shown) such that activation of the handpiece may withdraw actuation cannula (308) and actuation jaws (310) proximally relative to the rest of suture management device (300). As actuation jaws (310) are withdrawn proximally, they may engage cutter jaws (312). This engagement may cause cutter jaws (312), which may not slide relative to catheter section (304), to move toward the center of catheter section (304). As the cutter jaws (312) move toward each other, they may sever suture (316). The point at which cutter jaws (312) sever suture (316) may control the length of suture that remains beyond a surgical knot, for example, and it should be appreciated that the configuration of suture management device (300) may be altered to achieve a desirable cutting length.

While shown in FIG. 3 as being fixed relative to catheter section (304), cutter jaws (312) may be engagable with a handpiece (not shown) to slide relative catheter section (304). In these variations, the actuation cannula (308) may be fixed to catheter section (304), and may decrease in diameter from the distal end of actuation cannula (308) to the proximal end of actuation cannula (308). When the handpiece is used to withdraw cutter jaws (312) proximally relative to suture management device (300), the cutter jaws (312) may engage actuation cannula (308). This may bring cutter jaws (312) together, and thereby cut suture (316).

While the variation of suture management device (300) shown in FIG. 3 utilizes an actuator cannula that is withdrawn proximally relative to the catheter section, the actuator cannula may alternatively be configured to be pushed distally relative to the catheter section. Indeed, FIG. 4 shows a cross-sectional side view of one such variation of suture management device (400), including catheter section (402). Shown there are cutter jaws (404) attached to actuation cannula (406), suture channel (408), and actuator jaws (410) fixed to catheter section (402). Also shown there is suture (412). Again, actuation cannula (406) may be able to slide relative to catheter section (402). In some variations, actuation cannula (406) may engage a handpiece (not shown) such that activation of the handpiece causes the actuation cannula (406) to slide distally relative to catheter section (402). As actuation cannula (406) slides distally, the cannula may engage actuator jaws (410). This engagement may cause cutter jaws (404) to move toward each other, which may in turn sever suture (412).

While shown in FIGS. 3-4 as having two cutting jaws, the cutting assembly may have any number of cutting jaws. Indeed, the cutting assembly may have one, two, three, or four or more cutting jaws. In some variations, as will be described in more detail below, the cutting assembly includes alternative methods of cutting and does not include any cutting jaws. Indeed, while shown in FIGS. 3-4 as having cutting jaws, the cutting assemblies described here may have any suitable cutting structure. For example, the cutting assembly may include one more cantilevered cutting blade. FIG. 5 shows a cross-sectional side view of distal portion of one such variation of suture management device (500). Shown there is suture engagement portion (502) including suture channel (504), cantilever cutting blade (506) having blade edge (508), and balloon (510) having balloon lumen (512). Generally, cantilever cutting blade (506) may move between a standby position (not shown) to a cutting position where the blade edge (508) passes at least partially through suture channel (504).

To sever a suture (not shown) disposed within suture channel (504), balloon (510) may be inflated. The increase in volume of balloon (510) may bias cantilever cutting blade (506) away from the outer wall (514) of suture engagement portion (502), thereby moving cantilever cutting blade (506) to its cutting position, as shown in FIG. 5. Balloon (510) may be inflated by passing a fluid through balloon lumen (512) into balloon (510). This fluid may be any suitable gas or liquid. In some variations, cantilever cutting blade (506) may naturally return to its standby position when the balloon is deflated. In other variations, balloon (510) is attached to both cantilever cutting blade (506) and outer wall (514) of suture engagement portion (502), such that deflation of balloon (510) returns cantilever cutting blade (506) to its standby configuration. In still other variations, suture management device (500) may include some structure to return cantilever cutting blade (506) to its standby position when balloon (510) is deflated. In some of these variations, suture management device (500) comprises one or more springs that bias cantilever cutting blade (506) away from the cutting position. In others of these variations, suture management device (500) comprises one or more magnets that bias cantilever cutting blade (506) away from the cutting position.

While shown in FIGS. 3-5 as having cutting blades or jaws with cutting surfaces that are oriented approximately perpendicular to the longitudinal axis of the suture management device, the cutting assemblies may have cutting blades or jaws that are oriented at any angle relative to the suture management device. FIG. 6 illustrates a cross-sectional side view of one such variation of suture management device (600), including suture engagement portion (602) attached to catheter section (604). Shown there is blade housing (608) attached to longitudinally oriented blade (606) and inner shaft (610). Also shown there is suture (612) disposed at least partially within suture engagement portion (602). In variations such as these, blade housing (608) may be able to slide within suture engagement portion (602). Similarly, inner shaft (610) and plunger (614) may be able to slide within suture engagement portion (602) and catheter section (604). Additionally, inner shaft (610) may be engagable with blade housing (608) and a handpiece (not shown), such that activation of the handpiece causes inner shaft (610) to move distally relative to the suture management device (600). This in turn may move the inner shaft (610), plunger (614), and suture (612) distally relative to the suture management device (600), and may cause blade (606) to sever suture (612). Additionally, activation of the handpiece may be used to cause blade housing (608) to move proximally relative to suture management device (600). This in turn may move blade (606) proximally relative to suture management device (600), and may cause blade (606) to sever suture (612). While shown in FIG. 6 as configured to push inner shaft (610), plunger (614), and suture (612) distally relative to suture management device (600) to sever a suture (612), suture management device (600) may alternatively be configured to pull blade (606) proximally to sever a suture.

FIGS. 7A and 7B show another variation of suture management device (700) having cutting assembly (702) with a longitudinally oriented blade (704). Shown there is suture engagement portion (706) defining a suture channel (708), blade housing (710) attached to blade (704) and spring (714), balloon (716) having a balloon lumen (718), and catheter section (720). Blade housing (710) may be capable of sliding within catheter section (720). When balloon (716) is deflated, blade housing (710) may sit in a standby position, as shown in a cross-sectional side view in FIG. 7A. In order to activate suture management device (700), balloon (716) may be inflated by passing a fluid, either liquid or gas, through balloon lumen (718). The inflated balloon (716) may push blade housing (710) distally relative to catheter section (720). This may in turn move blade (704) distally through blade channel (722) in suture engagement portion (706), as shown in FIG. 7B. As blade (704) moves through blade channel (722), it may also move through suture channel (708) and may thereby sever a suture (not shown). Once balloon (716) is deflated, spring (714) may act to return blade housing (710) to its standby position. Similarly, suture management device (700) may alternatively or additionally include magnets or other structures that act to return blade housing (710) to its standby position.

FIGS. 8A and 8B show still another variation of a suture management device (800) having cutting assembly (802) with a longitudinally oriented blade (804). Shown there is suture engagement portion (806) defining a suture channel (808), return magnet (810), blade housing (812) including housing magnet (814) and attached to blade (804), catheter section (816), and actuator rod (818) having actuator magnet (820). Blade housing (812) and actuator rod (818) may be able to slide within catheter section (816). Furthermore, the magnets may be axially magnetized and oriented such that housing magnet (814) is repelled by both return magnet (810) and actuator magnet (820). Additionally, the magnets may be configured such that the repulsive force between the housing magnet (814) and the actuator magnet (820) is stronger than the repulsive force between housing magnet (814) and return magnet (810). When cutting assembly (802) is not being activated, blade housing (812) may be in a standby position, as shown in a cross-sectional side view in FIG. 8A. Actuator rod (818) may be engagable with a handpiece (not shown), such that activation of the handpiece causes actuator rod (818) to slide distally relative to catheter section (816). As actuator rod (818) moves distally, the repulsive force between actuator magnet (818) and housing magnet (814) may cause blade housing (812) to slide distally relative to catheter section (816), and may overcome the repulsive force between housing magnet (814) and return magnet (810). This may in turn cause blade (804) to move distally within blade channel (822), as shown in FIG. 8B. This movement may result in blade (804) severing a suture (not shown). When the handpiece is no longer activated, and actuator rod (818) returns to its original position, the repulsive force between housing magnet (814) and return magnet (810) may cause blade housing (812) to return to its standby position. Alternatively or additionally, a return spring or other structure may act to return blade housing (812) to its standby position.

Figure 9A:
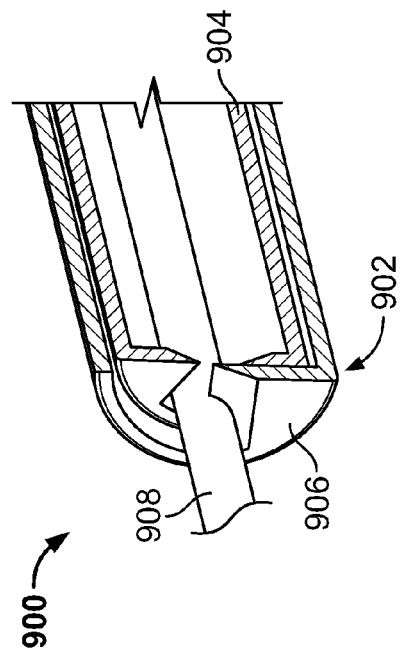
FIGS. 9A is a cross-sectional side view of a suture management device having a cutting assembly with cutting apertures.
Figure 9B:
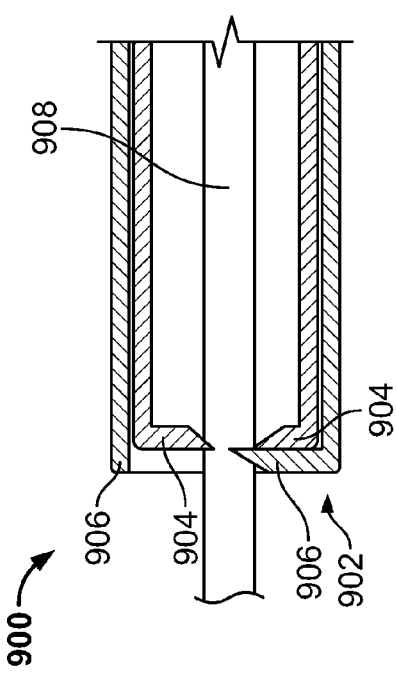
FIGS. 9B-9D are perspective views of the suture management device of FIG. 9A.
Figure 9C:
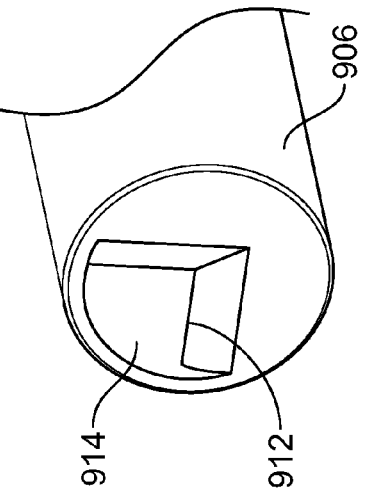
Figure 9D:
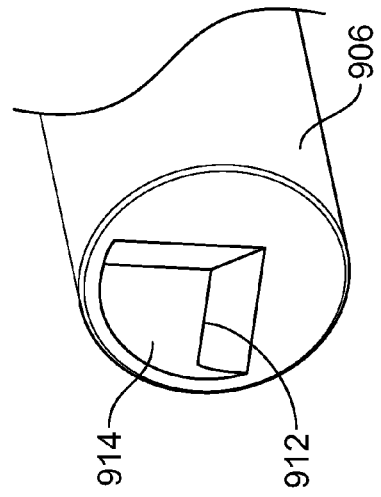

FIGS. 9A-9D show another variation of suture management device (900) having cutting assembly (902). FIGS. 9A and 9B shows a cross-sectional side view and a cross-sectional perspective view, respectively, of suture management device (900) including inner cannula (904) and outer cannula (906). Also shown there is suture (908). Inner cannula (904) may be disposed within outer cannula (906), and may be capable of rotating relative to outer cannula (906). Additionally, inner cannula (904) may define an inner aperture (910), which may in turn have cutting edges (912), as shown in a perspective view in FIG. 9C. Similarly, outer cannula (904) may define an outer aperture (914), which may also have cutting edges (912), as shown in a perspective view in FIG. 9D.

Inner cannula (904) and outer cannula (906) may be aligned such that at least a portion of inner aperture (910) aligns with at least a portion of outer aperture (914), enabling suture (908) to pass through the inner (910) and outer (914) apertures. When inner cannula (904) is rotated relative to outer cannula (906), the cutting edges (912) of the inner (910) and outer (914) apertures are brought together, thereby decreasing the amount of overlap between inner (910) and outer (914) apertures, which may in turn sever suture (908).

While shown in FIGS. 9A-9D as having quarter-circle shapes, inner (910) and outer (914) apertures may have any size and shape. Indeed, inner (910) and outer (914) apertures may have a shape that approximates a circle, a half-circle, a triangle, a rectangle, an oval, a polygon, sections thereof or the like. Additionally, while shown in FIGS. 9A-9D as having the same size and shape, inner (910) and outer (914) apertures need not have the same size and shape. Indeed, inner (910) and outer (914) apertures may have the same shape but different sizes, may have different shapes but the same size, or may have different shapes and different sizes.

It should be appreciated that each cutting assembly may include any feature or combination of features as described above. Indeed, the cutting assemblies may include any number of cutting jaws, blades, apertures with cutting edges, combinations thereof and the like, and may be activated using magnets, balloons, actuator cannulas, rotating cannulas, combinations thereof or the like.

Handpieces

The handpieces described here may have any suitable configuration of elements. Generally, the handpiece may allow a user to guide or manipulate the suture management device within a body or enclosed space. The handpiece may further allow a user to guide or manipulate a suture at a location remote from the user. Additionally, the handpiece may control the actuation of one or more cutting assemblies, which may be used to sever a suture or a suture knot.

Figure 10A:
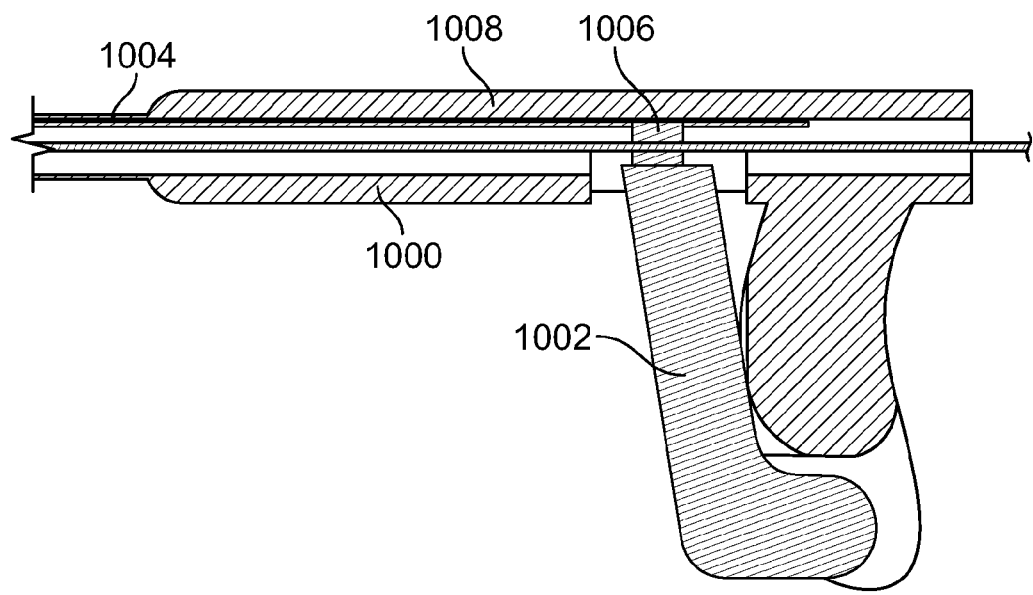
FIGS. 10A and 10B are side views of variations of handpieces having actuator handles.

In some variations, the handpiece may comprise one or more actuation handles. FIG. 10A shows one such variation of handpiece (1000) comprising actuation handle (1002) and connected to catheter section (1004). Also shown there is connection sleeve (1006), actuation cannula (1008). Connection sleeve (1006) may connect actuation handle (1002) to actuation cannula (1008), which may in turn cause actuation cannula (1008) to move when actuation handle (1002) is squeezed. Actuation handle (1002) may provide a structure that is easily graspable by a user. Additionally, actuation handle (1002) may be used to control the severing of a suture (not shown), by activating a cutting assembly (not shown).

Figure 10B:
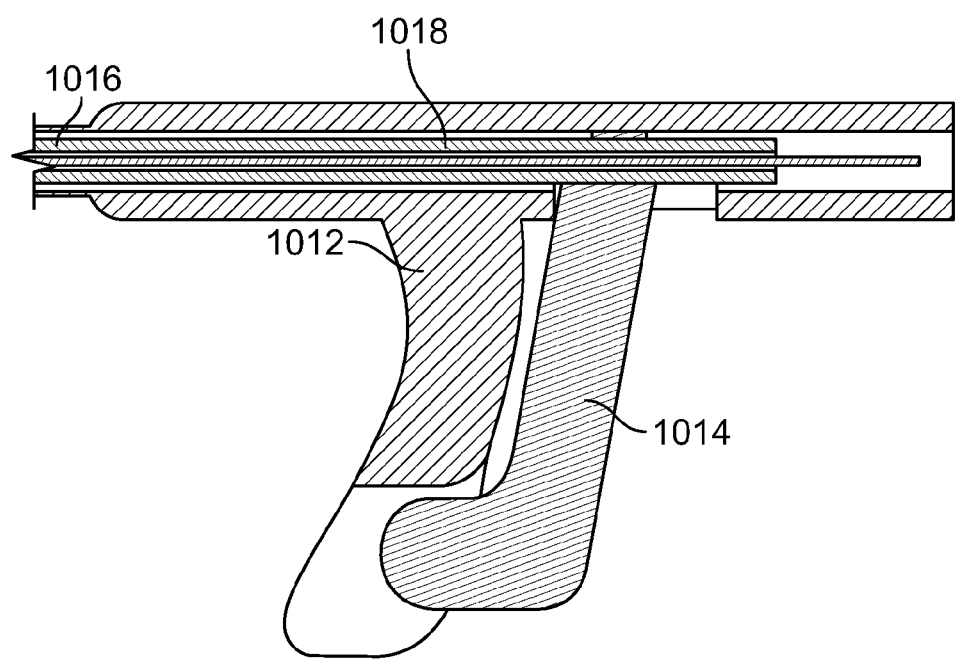

In some variations, such as that shown in FIG. 10A, the actuation handle (1002) is configured to pull an actuation cannula (1006) proximally relative to catheter section (1008) when the actuation handle (1002) is compressed. FIG. 10B shows another variation of handpiece (1012) comprising actuation handle (1014) and connected to catheter section (1016). In these variations, actuation handle (1014) is configured to push actuation cannula (1018) distally relative to catheter section (1016) when actuation handle (1014) is compressed. In still other variations, the actuation handle may be configured to rotate a cannula when the actuation handle is compressed.

Figure 11A:
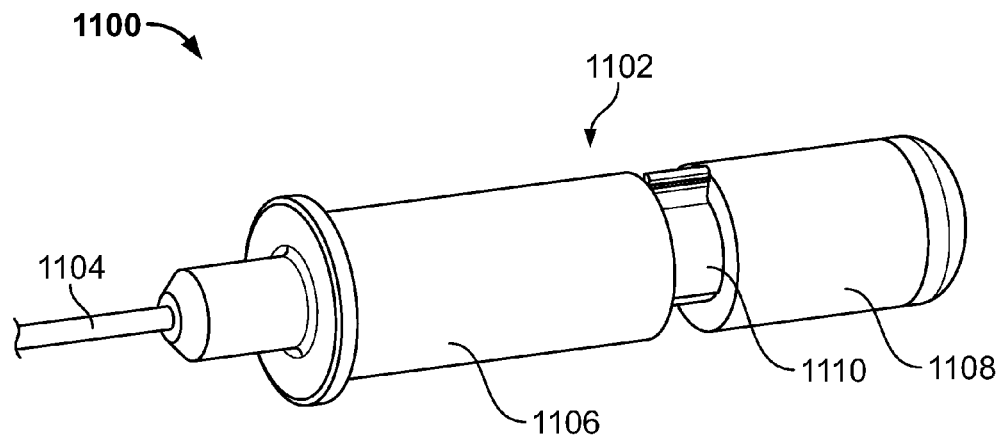
FIGS. 11A-11C are perspective views of a variation of a handpiece having a button and a safety lock.
Figure 11B:
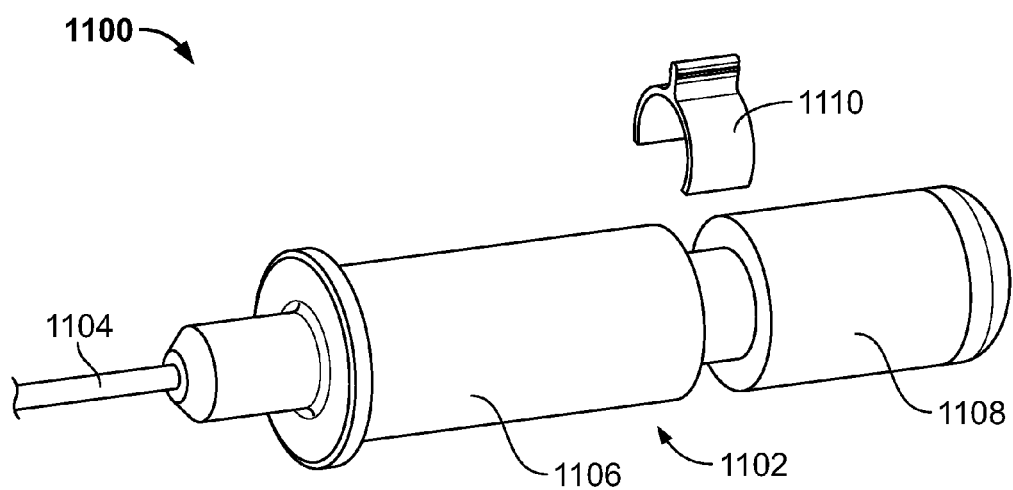
Figure 11C:
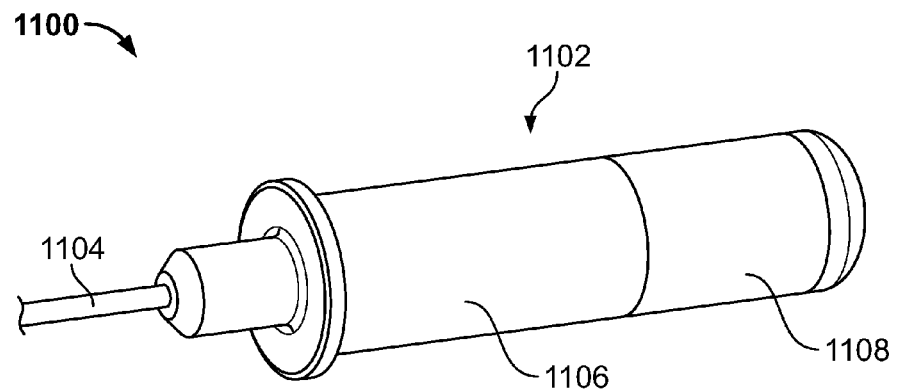
Figure 11D:
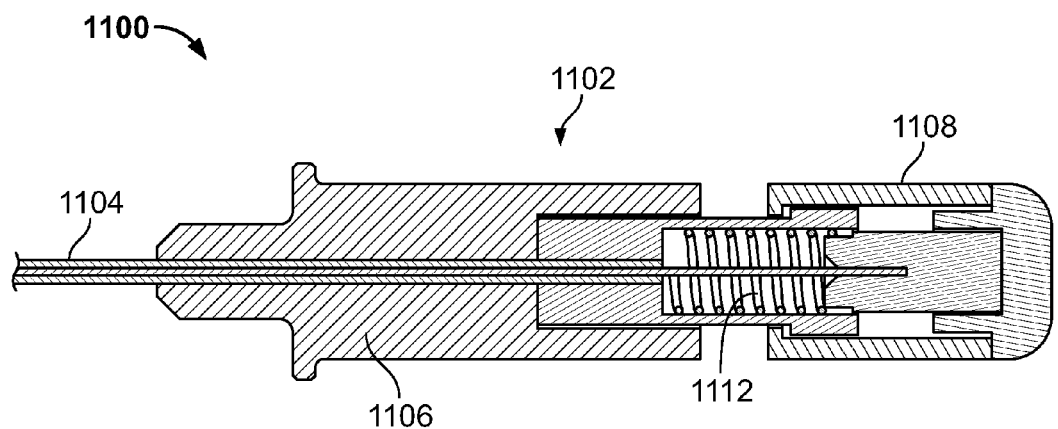
FIG. 11D is a cross-sectional side view of the handpiece of FIGS. 11A-11C.

Additionally, in some variations the handpiece may comprise one or more safety features or locks that may prevent a user from accidentally activating a cutting assembly. FIGS. 11A-11D illustrate a variation of suture management device (1100) comprising handpiece (1102) connected to catheter section (1104). FIG. 11A shows a perspective view of suture management device (1100), comprising handle portion (1106), button (1108), and safety lock (1110). In these variations, button (1108) may be depressed relative to handle portion (1106) to activate a cutting assembly (not shown), as shown in FIG. 11B. When safety lock (1108) engages handpiece (1102) as shown in FIG. 11A, however, button (1108) may not be depressed. In order to depress button (1108), safety lock (1110) must first be removed, as shown in FIG. 11C. Once the cutting assembly has been activated, a spring (1112) disposed within handpiece (1102) may return the button to its original position, as shown in a cross-sectional side view in FIG. 11D, and the safety lock (1110) may be returned to the device.

While shown in FIGS. 10-11B as having actuation handles or buttons, the handpiece may comprise any suitable structure that is capable of activating a cutting assembly. These structures include, but are not limited to triggers, sliding actuators, cranks, knobs, rotating handles, combinations thereof, and the like. Additionally, in variations where the suture management device comprises a retractable guide, as will be described in more detail below, the handpiece may additionally include one or more structures to retract retractable guide into the catheter section. The handle may also comprise a luer for attachment to one or more inflation lumens in the case of balloon actuating cutting mechanisms.

Suture Channels and Suture Engagement Portions

Generally, the suture management devices described here may comprise one or more suture channels through which one or more sutures may be passed. The suture channel may have ends positioned at any two suitable locations on the suture management device. The placement of the suture channel may be determined by the configuration of a cutting assembly or another feature of the device. In some variations, the suture passes through a suture channel that spans between the proximal and distal ends of the suture management device, as shown in FIGS. 1A and 1B. In other variations, the suture channel enters and exits the suture management device through a suture engagement portion or other aperture.

FIGS. 12A and 12B illustrate one variation of suture engagement portion (1200). FIG. 12A shows a perspective view and FIG. 12B shows a cross-sectional side view of suture engagement portion (1200). Shown there is suture channel (1202), cantilever cutting blade (1204) having blade edge (1206), and balloon (1208) having balloon lumen (1210). In this variation, suture channel has a suture entrance (1212) at the distal end of suture engagement portion (1200) and a suture exit (1214) in wall (1216) of suture engagement portion (1200). A suture (not shown) may be passed from suture entrance (1212) to suture exit (1214), or vice versa, thereby allowing suture engagement portion (1200) to engage a portion of a suture.

FIGS. 12A and 12B show suture engagement portion (1200) as having a structure that may be independent of a catheter section (not shown), but it need not. In some variations, the suture engagement portion may be integral with a catheter section. Additionally, the suture engagement portion may be located at any point along the device. In some variations, the suture engagement portion may be located at the distal end of the suture management device. In other variations, the suture engagement portion may be located at some point along the length of a catheter section.

Figure 13A:
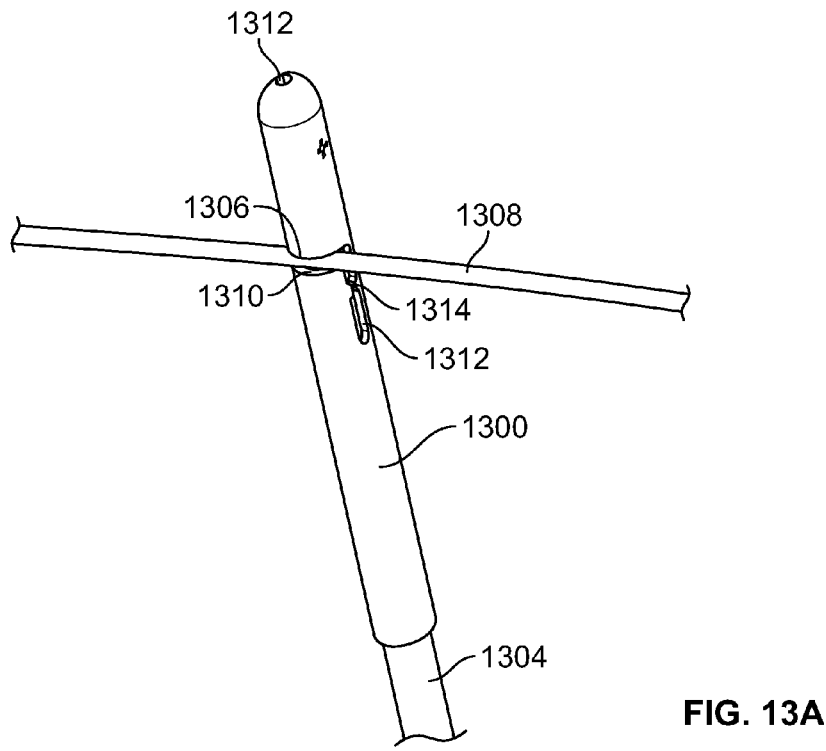
FIGS. 13A and 13B are perspective views of a suture engagement portion having a slot.
Figure 13B:
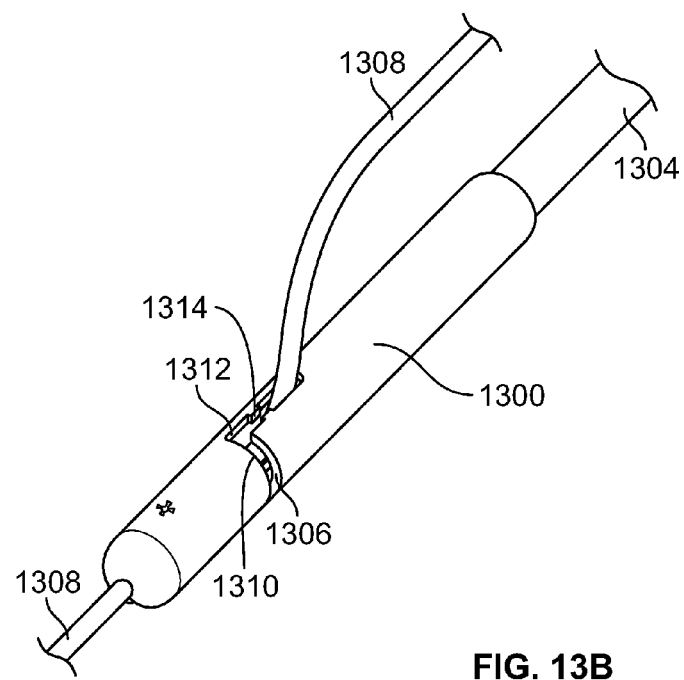

In some variations that include a suture engagement portion, the suture engagement portion may include one or more slots on the surface of suture engagement portion. These slots may allow the suture engagement portion to engage a portion of a suture without the need to pass one end of the suture through the suture channel. These variations may find particular utility in instances when no end of a suture is available, or a tangled section of suture would otherwise prevent engagement between the suture management device and a portion of the suture. FIGS. 13A and 13B show perspective views one such variation of suture engagement portion (1300). Shown there is suture engagement portion (1300) attached to catheter section (1304) and comprising slot (1306). Also shown there is suture (1308). Slot (1306) may comprise transverse segment (1310), longitudinal segments (1312), and suture tab (1314).

In order to engage suture engagement portion (1300), suture (1308) may be placed within transverse segment (1310), as shown in FIG. 13A. The suture (1308) may then be threaded through longitudinal segments (1312) and past suture tab (1314), such that suture (1308) enters the side of suture engagement portion (1300) and exits at the distal end of suture engagement portion (1300). Suture tab (1314) may serve to prevent suture (1308) from disengaging with suture engagement portion (1300) while the suture management device is manipulated or advanced.

While shown in FIGS. 13A and 13B as having both transverse (1310) and longitudinal (1312) segments, slot (1306) may have any suitable configuration. Indeed, slot (1306) may have any combination of linear or arced sections, and these sections may be oriented within suture engagement portion (1300) in any suitable configuration. Additionally, while shown in FIGS. 13A and 13B as sized to accept one suture (1308), slot (1306) may be sized to accept two, three or four or more sutures (1308). Furthermore, suture engagement portion (1300) may have any number of slots (1306), and each slot (1306) may have any number of suture tabs (1314). Generally, suture tab (1314) may be any structure that resists movement of a suture through slot (1306).

In variations in which the suture management device comprises one or more suture channels, these suture channels may have any suitable shape or configuration. In some variations, the suture channel may be configured such that bodily tissue is incapable of entering the suture channel. This may provide an additional level of safety as it may prevent tissue from contacting the cutting assembly. In some variations, the suture channel may be configured to accept only one suture. In other variations, the suture channel may be configured to accept two, three, or four or more sutures. In still other variations, the suture channel may be sized such that a suture may pass therethrough while a knotted section of the suture may not pass therethrough. In these variations, the suture management device may be able to push a knotted section of suture to a location remote from a user. In yet other variations, the suture channel may be sized to accept a retractable guide, as described in more detail below, and one or more sutures.

Figure 14A:
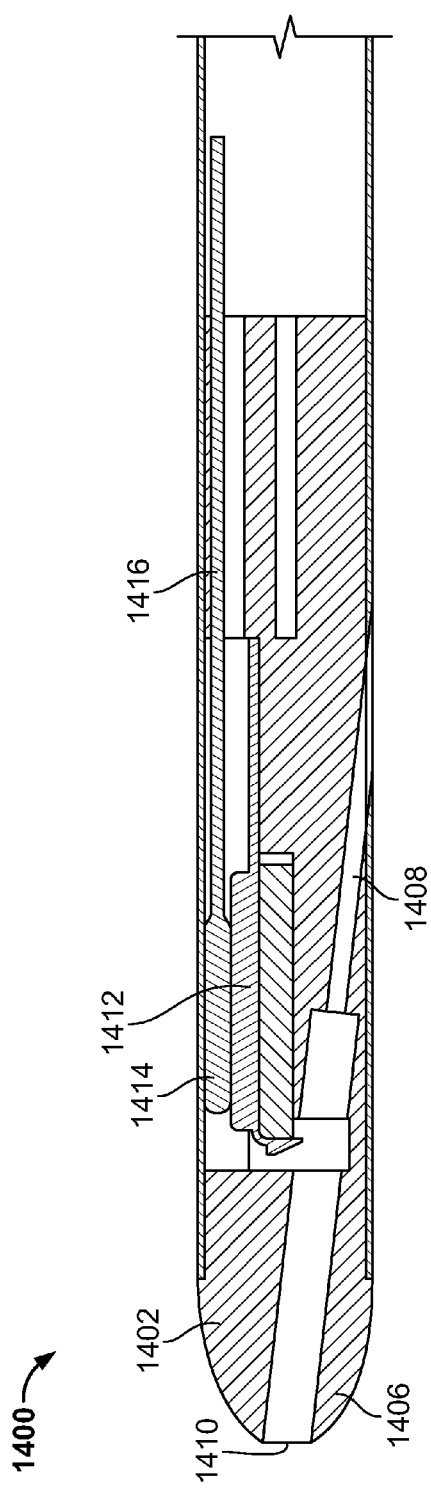
FIGS. 14A and 14B are cross-sectional side views of a suture management device that may sever a suture knot.
Figure 14B:
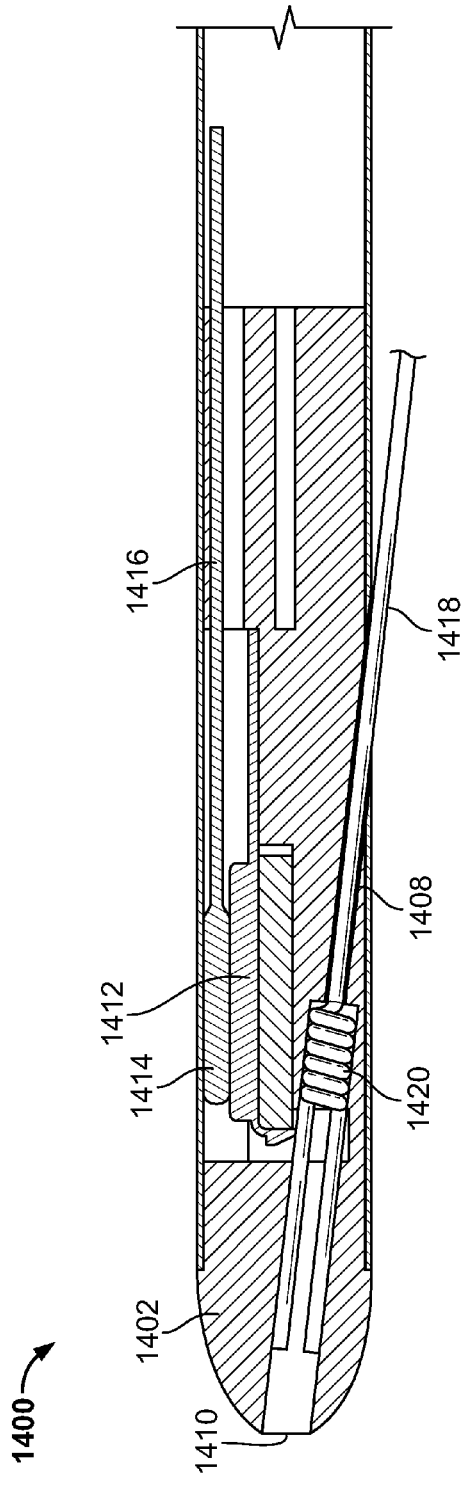

In some variations, the suture management device includes one or more features that allow a user to remove a suture knot in the event of an undesirable suturing outcome. FIGS. 14A and 14B show one such variation of suture management device (1400), including suture engagement portion (1402). More specifically, FIG. 14A shows a cross-sectional side view of suture management device (1400). Also shown there is suture channel (1406) having first section (1408) and second section (1410), cantilever blade (1412), and balloon (1414) with balloon lumen (1416). Second section (1410) of suture channel may sized such that a both a suture (1418) and a suture knot (1420) may pass therethrough, as shown in FIG. 14B. First section (1408) may be sized such that suture (1418) may pass therethrough, but suture knot (1420) may not. This may serve to position suture knot (1420) such that activation of cantilever blade (1412) will sever both suture (1418) and suture knot (1420).

Retractable Guide

Figure 15A:
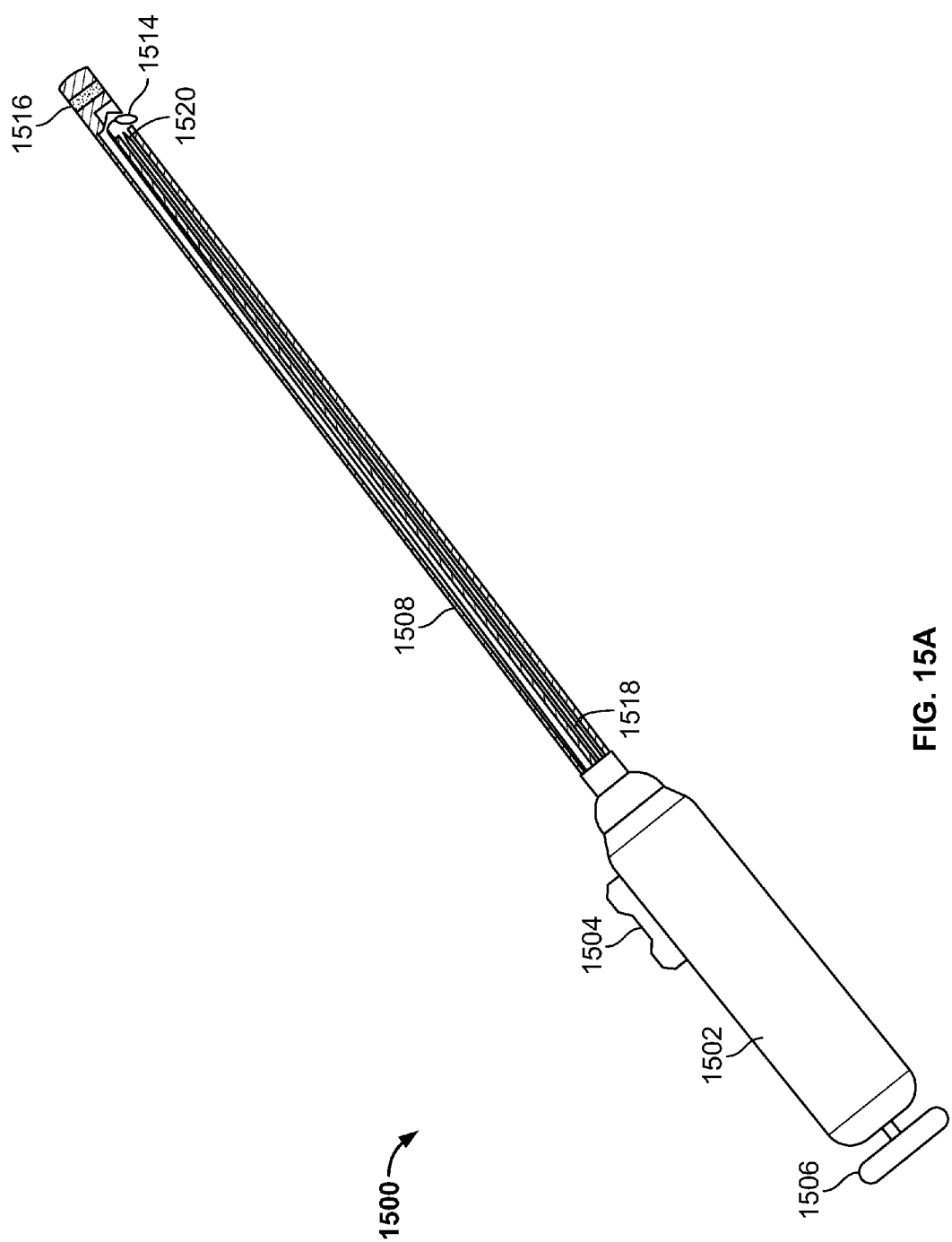
FIGS. 15A-15C are cross-sectional side views of a suture management device having a retractable guide with a guide loop.
Figure 15B:
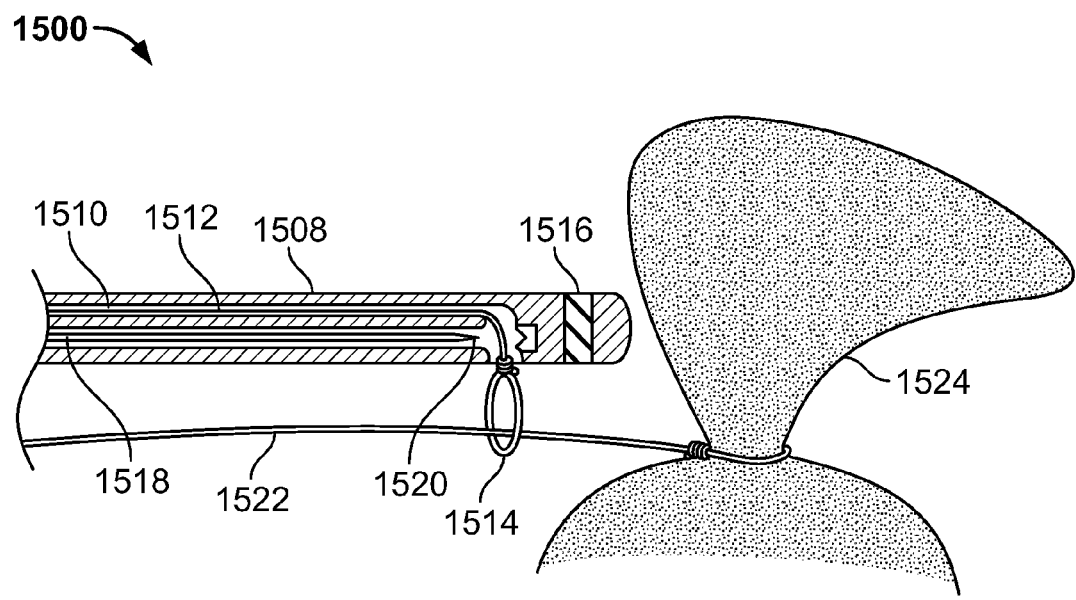
Figure 15C:
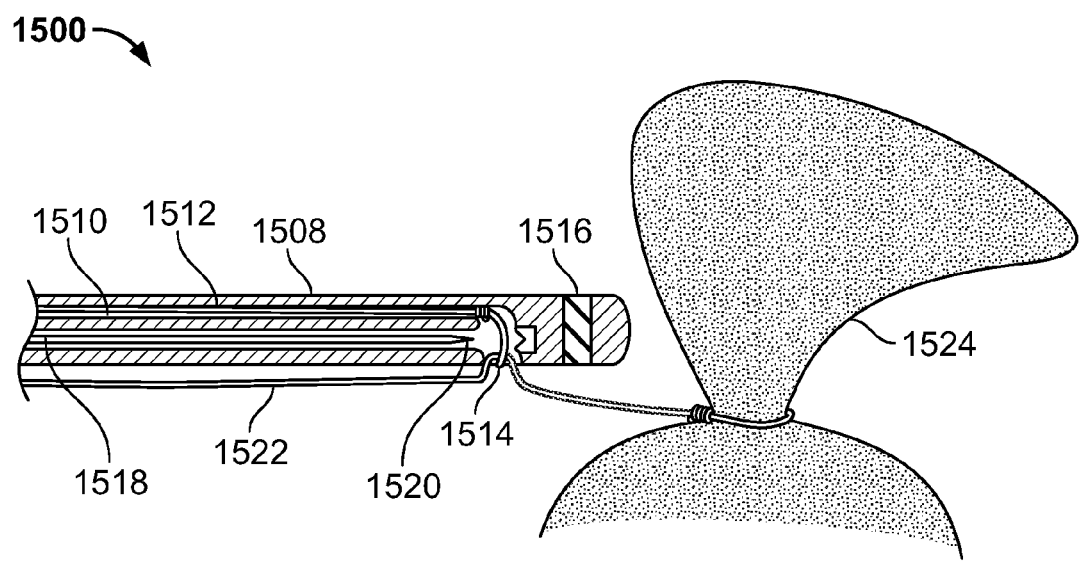

In some variations, the devices described here comprise a retractable guide. FIGS. 15A-15C illustrate a variation of suture management device (1500). FIG. 15A shows a perspective view of the entire suture management device (1500). Shown there is handpiece (1502) with sliding actuator (1504) and push actuator (1506), and catheter section (1508) having suture channel (1510), retractable guide (1512) with guide loop (1514), marker (1516), and push rod (1518) with blade (1520). Retractable guide (1512) may be disposed within suture channel (1510), and may be withdrawn proximally into suture channel (1510) upon activation of sliding actuator (1504). Similarly, blade (1520) may be advanced distally relative to catheter section (1508) upon activation of push actuator (1506).

To use suture management device (1500), a suture (1522) may be threaded through guide loop (1514), and suture management device (1500) may be advanced over suture (1522) to a target site (1524), as shown in FIG. 15B. In some variations, this advancement may be visualized using marker (1516) and/or imaging methods such as fluoroscopy or ultrasound to ensure suture management device (1500) is properly placed. Once suture management device (1500) has been properly placed, retractable guide (1512) may be withdrawn into suture channel (1510) using slide actuator (1504). This may in turn cause guide loop (1514) to engage suture (1522) and pull suture (1522) at least partially within suture channel (1510), as shown in FIG. 15C. Once suture (1522) has been pulled into suture channel (1510), blade (1520) may be advanced to sever suture (1522).

While shown in FIGS. 15A-15C as having a marker (1516), suture management device (1500) need not. In variations that do include a marker (1516), the marker (1516) may be made of any material that is capable of being viewed by an imaging method (e.g., fluoroscopy, ultrasound, etc.). Although shown in FIGS. 15A-15C as being located on the distal end of catheter section (1508), marker may be disposed anywhere in, on, or along suture management device (1500). Additionally, while shown in FIGS. 15A-15C as having only one marker, suture management device (1500) may have any number of markers. Indeed, suture management device (1500) may have zero, one, or two or more markers.

Figure 16:
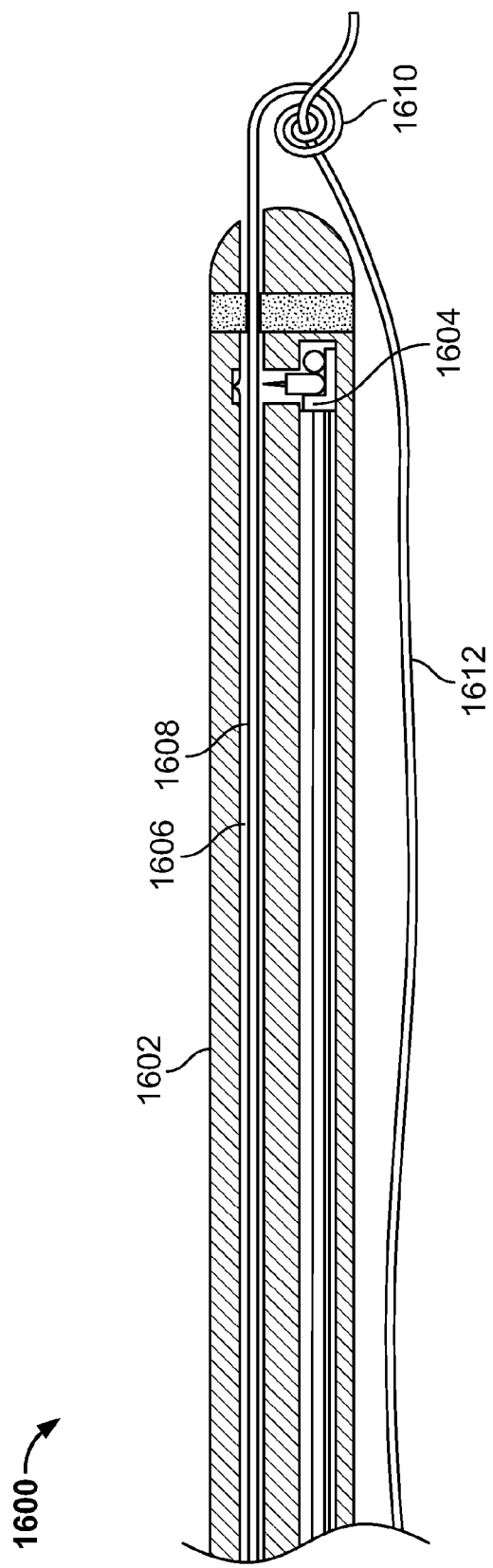
FIG. 16 is a cross-sectional side view of a suture management device having a rectrable guide with a spiral loop.

Additionally, while shown in FIGS. 15A-15C as having a guide loop (1514), the retractable guide (1512) may have any suitable structure for engaging suture (1522). Indeed, FIG. 16 shows another variation of suture management device (1600), having catheter section (1602) with cutting assembly (1604), suture channel (1606), and retractable guide (1608) having spiral loop (1610). Also shown there is suture (1612). Spiral loop (1610) may be wound around suture (1612) to engage suture, which may allow suture management device (1600) to engage suture (1612) without the need to thread one end of suture (1612) through the retractable guide (1608). This may provide particular utility in instances where neither end of the suture is available to be threaded through retractable guide (1608). Generally, the retractable guide may be any structure capable of being withdrawn into a suture channel, may be made of any suitable material, and may have any suitable geometry (e.g., one or more curves or bends). Examples of suitable materials include, but are not limited to nickel titanium alloys, stainless steel, PET, polyether block amide, and combinations thereof.

It should be appreciated that the devices described here may include any combination of elements of as described above. More specifically, the suture management devices may include any combination of handpieces, catheter sections, cutting assemblies, markers, and retractable guides as described above.

Methods

Any of the suture management devices described above may be used to sever a suture at a point remote from a user. In some methods, a suture is used in a procedure at a target location. This procedure may be any suitable procedure, including, but not limited to, wound closure, drawing together two tissue segments, and ligating an area of tissue such as the left atrial appendage. In some of these methods, a knot may then be tied at the target site. This knot may be any suitable knot, including but not limited to a slip knot. In some of these methods, a suture management device may engage at least a portion of the suture.

The suture management device may engage the suture in any suitable manner as described above, and this engagement may depend on the configuration of elements in the device. In variations where the suture management device includes a suture channel, a free end of the suture may be threaded through one end of the suture channel and passed through the other end. In variations in which the suture management device includes one or more slots, the suture may be threaded through suture channel via the one or more slots. In variations where the suture management device comprises a retractable guide, the retractable guide may engage the suture. For example, when the retractable guide comprises a guide loop, an end of the suture may be passed through the eye of the guide loop. Alternatively, in variations where the retractable guide includes a spiral loop, and the spiral loop may be wrapped around a portion of the suture, or an end of the suture may be passed through the spiral loop.

Once the suture management device has engaged the suture, the suture management device may be advanced along the suture to the target site. In some variations, the suture management device may be advanced to the target site simultaneously with engaging the suture. For example, in variations where the suture is threaded between the ends of a suture channel, the suture management device may be advanced toward the target site while the suture is being threaded. In some variations, the suture acts to guide the suture management device to the target location. Indeed, in variations that include a retractable guide, the engagement between the retractable guide and the suture may serve to lead the suture management along the length of the suture until it reaches the target site. Similarly, the suture management device may be advanced to the target site through one or more catheters or catheter assemblies, a sheath, or other introducer, which may or may not be engaged with the suture, and which may or may not include one or more curves or bends. In some of these methods, the suture management device may be advanced under fluoroscopic or ultrasonic guidance.

As the suture management device is advanced to the target site, a portion of the device may abut the knot. In some of these variations, the suture management device may hold the knot in place, yet still allow a portion of suture to move freely through the device. In some of these variations, a portion of suture may be withdrawn through the device relative to the knot. In some variations, this may serve to tighten the knot. In other variations, such as variations that include a slip knot, this may serve to cinch a loop of suture.

Once the desired knot tightness, and knot and suture placement has been achieved, the suture management device may then be activated to sever the suture. In some variations, activation of the suture management device results in the activation of a cutting assembly. It should be noted that any of the cutting assemblies as described above may be used to sever a suture. In variations that include a retractable guide, the retractable guide may first be withdrawn into the device, which may in turn pull a portion of the suture into the device, where it may be severed by the cutting assembly. In some variations, suture management devices may be used to remove a knot in the case of an undesirable suturing outcome. Additionally, the suture management device may be configured to sever a suture such that a predetermined amount of suture remains. In some variations, this may be achieved by configuring the cutting portion of the cutting assembly to sever a suture at a given distance from the distal end of the device. If the end of the suture management device is abutting the knot, a user may know how much suture will remain relative to the knot when the suture is severed. If a longer length of suture is desired, the cutting assembly may be reconfigured, or the user may withdraw the suture management device a certain amount relative to the suture (and thus the knot).

In some methods, a knot may be tied extracorporeally, and then advanced to the target site. In other methods, a suture management device may be used to advance the knot to the target site. In these methods, the suture management device may engage at least a portion of the suture as described above. Generally, a portion of the suture management device may abut or otherwise contact the knot such that as the suture management device is advanced, it pushes the knot. As such, the knot may be pushed to the target location by the suture management device. In some of these variations, a portion of the suture may act to guide the suture management device to the target site. Of course, as described above, the suture management device may also be advanced to the target site through one or more catheters or catheter assemblies, a sheath, or other introducer, which may or may not be engaged with the suture, and which may or may not include one or more curves or bends. In these or other variations, the suture management device may be advanced under fluoroscopic or ultrasonic guidance. Once the knot has been positioned at the target sit, it may be tightened or removed, as described above. Similarly, once the proper tightness has been achieved, the suture management device may sever the suture, as described above.

In still other methods, the suture management devices described here may be used to ligate a portion of tissue, such as the left atrial appendage. In these variations, one end of a suture may be tied to itself using a slip knot or similar knot to create a loop. A suture management device may engage the suture in any of the ways as described above, and the suture management device may be used to guide the loop to a target location. Again, the suture management device may be advanced to the target site through one or more catheters or catheter assemblies, sheaths, or other introducers. In some methods, this advancement may occur under fluoroscopic or ultrasonic visualization. Once at the target site, the loop may be placed around the tissue to be ligated. In some variations, the suture management device may be manipulated to place the loop around the target tissue. In other variations, one or more additional tools may be advanced to the target location to help place the loop around the target tissue. Once in place, one end of the suture may be withdrawn through the suture management device to cinch the tissue. The knot and suture may be removed in the case of an undesirable suturing outcome, otherwise the knot may be tightened and the suture severed as described above.

While devices and methods have been described in some detail here by way of illustration and example, such illustration and example may be for purposes of clarity of understanding only. It will be readily apparent to those of ordinary skill in the art in light of the teachings herein that certain changes and modifications may be made thereto without departing from the spirit and scope of the appended claims.

What is claimed is:

1. A device for severing a portion of a suture comprising:
    an elongate tubular member having a proximal end, a distal end, and a lumen at least partially therebetween, the elongate tubular member comprising an aperture in a wall thereof for passage of a suture therethrough;
    a plunger attached to an inner shaft, the inner shaft slidably disposed within the elongate tubular member and the plunger fully disposed within the lumen of the elongate tubular member;
    a blade connected to a blade housing and disposed within the lumen, wherein the blade is oriented parallel to the longitudinal axis of the lumen such that a cutting edge of the blade faces the plunger; and
    a handle, wherein the handle is configured to move the inner shaft, plunger, and suture distally relative to the lumen and the blade, such that the plunger pushes the suture into contact with the cutting edge of the blade to sever the suture.

2. The device of claim 1, wherein the handle comprises one or more safety features.

3. The device of claim 1, further comprising a retractable guide.

4. The device of claim 1 wherein the aperture comprises a transverse slot segment and at least one longitudinal slot segment.

5. The device of claim 4 wherein the at least one longitudinal slot segment comprises a suture tab configured to prevent disengagement of the suture during advancement of the device.

* * * * *